United States Patent
Napolitano et al.

(10) Patent No.: US 8,672,846 B2
(45) Date of Patent: *Mar. 18, 2014

(54) CONTINUOUS TRANSMIT FOCUSING METHOD AND APPARATUS FOR ULTRASOUND IMAGING SYSTEM

(75) Inventors: David J. Napolitano, Pleasanton, CA (US); Brian Derek DeBusschere, Orinda, CA (US); Glen W. McLaughlin, San Carlos, CA (US); Larry Y. L. Mo, San Ramon, CA (US); Ching-Hua Chou, Mountain View, CA (US); Ting-Lan Ji, San Jose, CA (US); Robert W. Steins, Santa Clara, CA (US)

(73) Assignee: Zonare Medical Systems, Inc., Mountain View, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/196,748

(22) Filed: Aug. 2, 2011

(65) Prior Publication Data

US 2012/0083695 A1 Apr. 5, 2012

Related U.S. Application Data

(63) Continuation of application No. 11/492,471, filed on Jul. 24, 2006, now Pat. No. 8,002,705.

(60) Provisional application No. 60/701,812, filed on Jul. 22, 2005.

(51) Int. Cl.
*A61B 8/00* (2006.01)

(52) U.S. Cl.
USPC ........... 600/437; 600/407; 600/438; 600/441; 600/442; 600/443; 600/444; 600/445; 600/447; 600/453

(58) Field of Classification Search
USPC ......... 600/407, 437, 438, 441, 442, 443, 444, 600/445, 447, 453
See application file for complete search history.

(56) References Cited

U.S. PATENT DOCUMENTS 4,265,126 A 5/1981 Papadofrangakis
4,604,697 A 8/1986 Luthra
(Continued)

FOREIGN PATENT DOCUMENTS

WO 2008/051738 A2 5/2008

OTHER PUBLICATIONS

Anderson, M.E., et al., "The Impact of Sound Speed Errors on Medical Ultrasound Imaging", J. Acous. Soc. of Am., Jun. 2000, pp. 3540-3548, vol. 107, No. 6.
Freeman, S., "Retrospective Dynamic Transmit Focusing", Ultrasonic Imaging 17, 1995, pp. 173-196.
(Continued)

*Primary Examiner* — James Kish
(74) *Attorney, Agent, or Firm* — Kilpatrick Townsend & Stockton LLP

(57) ABSTRACT

In one embodiment, an ultrasound imaging method comprises: providing a probe that includes one or more transducer elements for transmitting and receiving ultrasound waves; generating a sequence of spatially distinct transmit beams which differ in one or more of origin and angle; determining a transmit beam spacing substantially based upon a combination of actual and desired transmit beam characteristics, thereby achieving a faster echo acquisition rate compared to a transmit beam spacing based upon round-trip transmit-receive beam sampling requirements; storing coherent receive echo data, from two or more transmit beams of the spatially distinct transmit beams; combining coherent receive echo data from at least two or more transmit beams to achieve a substantially spatially invariant synthesized transmit focus at each echo location; and combining coherent receive echo data from each transmit firing to achieve dynamic receive focusing at each echo location.

30 Claims, 12 Drawing Sheets

(56) References Cited

U.S. PATENT DOCUMENTS

| | | | |
|---|---|---|---|
| 4,852,576 A | 8/1989 | Inbar et al. | |
| 4,852,577 A | 8/1989 | Smith et al. | |
| 5,161,535 A | 11/1992 | Short | |
| 5,260,871 A | 11/1993 | Goldberg | |
| 5,269,289 A | 12/1993 | Takehana | |
| 5,313,948 A | 5/1994 | Murashita et al. | |
| 5,357,962 A | 10/1994 | Green | |
| 5,357,965 A | 10/1994 | Hall et al. | |
| 5,365,929 A | 11/1994 | Peterson | |
| 5,409,010 A | 4/1995 | Beach et al. | |
| 5,415,173 A | 5/1995 | Miwa et al. | |
| 5,417,215 A | 5/1995 | Evans et al. | |
| 5,555,534 A * | 9/1996 | Maslak et al. | 367/135 |
| 5,566,674 A | 10/1996 | Weng | |
| 5,579,768 A | 12/1996 | Klesenski | |
| 5,581,517 A | 12/1996 | Gee et al. | |
| 5,617,862 A | 4/1997 | Cole et al. | |
| 5,623,928 A * | 4/1997 | Wright et al. | 600/447 |
| 5,654,509 A | 8/1997 | Miele et al. | |
| 5,690,111 A | 11/1997 | Tsujino | |
| 5,720,289 A | 2/1998 | Wright et al. | |
| 5,776,063 A | 7/1998 | Dittrich et al. | |
| 5,782,766 A | 7/1998 | Weng et al. | |
| 5,799,111 A | 8/1998 | Guissin | |
| 5,857,973 A | 1/1999 | Ma et al. | |
| 5,935,074 A | 8/1999 | Mo et al. | |
| 5,954,653 A | 9/1999 | Hatfield et al. | |
| 5,984,870 A | 11/1999 | Giger et al. | |
| 5,993,393 A | 11/1999 | Ryan et al. | |
| 6,016,285 A | 1/2000 | Wright et al. | |
| 6,036,643 A | 3/2000 | Criton et al. | |
| 6,042,545 A | 3/2000 | Hossack et al. | |
| 6,068,598 A | 5/2000 | Pan et al. | |
| 6,069,593 A | 5/2000 | Lebby et al. | |
| 6,102,859 A | 8/2000 | Mo | |
| 6,110,119 A | 8/2000 | Hall | |
| 6,113,544 A | 9/2000 | Mo | |
| 6,120,446 A | 9/2000 | Ji et al. | |
| 6,142,943 A | 11/2000 | Mo et al. | |
| 6,162,176 A | 12/2000 | Washburn et al. | |
| 6,193,663 B1 * | 2/2001 | Napolitano et al. | 600/447 |
| 6,221,020 B1 | 4/2001 | Lysyansky et al. | |
| 6,263,094 B1 | 7/2001 | Rosich et al. | |
| 6,312,385 B1 | 11/2001 | Mo et al. | |
| 6,315,728 B1 | 11/2001 | Muzilla et al. | |
| 6,322,509 B1 | 11/2001 | Pan et al. | |
| 6,358,205 B1 | 3/2002 | Ustuner et al. | |
| 6,390,983 B1 | 5/2002 | Mo et al. | |
| 6,398,733 B1 | 6/2002 | Simopoulos et al. | |
| 6,423,003 B1 | 7/2002 | Ustuner et al. | |
| 6,434,262 B2 | 8/2002 | Wang | |
| 6,450,959 B1 | 9/2002 | Mo et al. | |
| 6,464,637 B1 | 10/2002 | Criton et al. | |
| 6,464,640 B1 | 10/2002 | Guracar et al. | |
| 6,464,641 B1 | 10/2002 | Pan et al. | |
| 6,468,218 B1 | 10/2002 | Chen et al. | |
| 6,491,636 B2 | 12/2002 | Chenal et al. | |
| 6,497,661 B1 | 12/2002 | Brock-Fisher | |
| 6,503,203 B1 | 1/2003 | Rafter et al. | |
| 6,512,854 B1 | 1/2003 | Mucci et al. | |
| 6,547,737 B2 | 4/2003 | Njemanze | |
| 6,577,967 B2 | 6/2003 | Mo et al. | |
| 6,679,847 B1 | 1/2004 | Robinson et al. | |
| 6,860,854 B2 | 3/2005 | Robinson et al. | |
| 6,926,671 B2 | 8/2005 | Azuma et al. | |
| 6,932,770 B2 | 8/2005 | Hastings et al. | |
| 6,980,419 B2 | 12/2005 | Smith et al. | |
| 7,022,075 B2 | 4/2006 | Grunwald et al. | |
| 7,627,386 B2 | 12/2009 | Mo et al. | |
| 8,002,705 B1 | 8/2011 | Napolitano et al. | |
| 2004/0068188 A1 | 4/2004 | Robinson et al. | |
| 2004/0179332 A1 | 9/2004 | Smith et al. | |
| 2006/0074320 A1 * | 4/2006 | Yoo et al. | 600/472 |
| 2006/0079778 A1 | 4/2006 | Mo et al. | |
| 2008/0146922 A1 | 6/2008 | Steins et al. | |
| 2010/0189329 A1 | 7/2010 | Mo et al. | |

OTHER PUBLICATIONS

Gammelmark, K.L., et al. "Multi-Element Synthetic Transmit Aperture Imaging using Temporal Encoding", 2002 SPIE Medical Imaging Meeting, Ultrasonic Imaging and Signal Processing, 2002; pp. 25-36.

Haider, B., "Synthetic Transmit Focusing for Ultrasound Imaging", 2000 IEEE Ultrasonics Symposium, pp. 1215-1218.

Haun, Mark Alden, "New Approached to Aberration Correction in Medical Ultrasound Imaging", Ph.D. Thesis, University of Illinois at Urbana-Champaign, 2003, 134 pages.

Hergum, T., et al., "Parallel Beamforming using Synthetic Transmit Beams", 2004 IEEE International Ultrasonics, Ferroelectrics, and Frequency Control Joint 50th Anniversary Conference, pp. 1401-1404.

Jellins, J. et al., "Velocity compensation in water-coupled breast echography", *Ultrasonics*, Sep. 1973, pp. 223-226.

Liu, D., et al., "Adaptive Ultrasonic Imaging Using SONOLINE Elegra™", 2000 IEEE Ultrasonics Symposium, 4 pages.

Nitzpon, P., et al., "New Pulsed Wave Doppler Ultrasound System to Measure Blood Velocities Beyond the Nyquist Limit," 1995, IEEE Transactions Ultrasonics and Ferroelectrics, and Frequency Control, vol. 42, No. 2, pp. 265-279.

Nock, L., et al., "Phase aberration correction in medical ultrasound using speckle brightness as a quality factor", J. Acous. Soc. Am., May 1989, vol. 85, No. 5, pp. 1819-1833.

Robinson, B., et al., "Synthetic Dynamic Transmit Focus", 2000 IEEE Ultrasonics Symposium, pp. 1209-1214.

Tortoli, P., et al., "Velocity Profile Reconstruction Using Ultrafast Spectral Analysis of Doppler Ultrasound," IEEE Transactions Sonics and Ultrasonics, Jul. 1985, vol. SU-32, No. 4, pp. 555-561.

International Search Report and Written Opinion of Apr. 3, 2008 for PCT Application No. PCT/US07/81253, 9 pages.

U.S. Appl. No. 11/586,212, filed Oct. 24, 2006.

Non-Final Office Action of Aug. 3, 2010 for U.S. Appl. No. 11/586,212, 8 pages.

Non-Final Office Action of Apr. 26, 2011 for U.S. Appl. No. 11/586,212, 15 pages.

Final Office Action of Mar. 9, 2012 for U.S. Appl. No. 11/586,212, 10 pages.

Non-Final Office Action of Sep. 14, 2007 for U.S. Appl. No. 10/961,709, 6 pages.

Non-Final Office Action of Dec. 2, 2008 for U.S. Appl. No. 10/961,709, 4 pages.

Notice of Allowance of May 15, 2009 for U.S. Appl. No. 10/961,709, 8 pages.

U.S. Appl. No. 11/492,557, filed Jul. 24, 2006.

Non-Final Office Action of Feb. 3, 2009 for U.S. Appl. No. 11/492,557, 15 pages.

Final Office Action of Oct. 27, 2009 for U.S. Appl. No. 11/492,557, 14 pages.

Non-Final Office Action of Aug. 17, 2011 for U.S. Appl. No. 11/492,557, 18 pages.

Final Office Action of Apr. 12, 2012 for U.S. Appl. No. 11/492,557, 14 pages.

Non-Final Office Action of Jun. 24, 2010 for U.S. Appl. No. 11/492,471, 11 pages.

Notice of Allowance of Apr. 13, 2011 for U.S. Appl. No. 11/492,471, 15 pages.

Non-Final Office Action of Nov. 5, 2010 for U.S. Appl. No. 12/628,169, 8 pages.

U.S. Appl. No. 12/340,578, filed Dec. 19, 2008.

Non-Final Office Action of Feb. 16, 2012, for U.S. Appl. No. 13/101990, 8 pages.

Notice of Allowance of Sep. 18, 2012, for U.S. Appl. No. 13/101990, 8 pages.

Non-Final Office Action of Sep. 14, 2012 for U.S. Appl. No. 12/340,578, 13 pages.

* cited by examiner

CONTINUOUS TRANSMIT FOCUSING METHOD AND APPARATUS FOR ULTRASOUND IMAGING SYSTEM

CROSS-REFERENCES TO RELATED APPLICATIONS

This application is a continuation of U.S. patent application Ser. No. 11/492,471, entitled "Continuous Transmit Focusing Method and Apparatus For Ultrasound Imaging System", filed on Jul. 24, 2006, now U.S. Pat. No. 8,002,705, issued Aug. 23, 2011, which claims priority to U.S. Provisional Patent Application No. 60/701,812, filed Jul. 22, 2005, the entire disclosures of which are incorporated herein by reference in their entirety for all purposes.

BACKGROUND OF THE INVENTION

This invention relates generally to ultrasound imaging systems and, more particularly, to continuous transmit focusing for ultrasound imaging systems.

Conventional ultrasound imaging systems generally form an image in the following manner. A short acoustic pulse is transmitted into a region of interest from a subset of transducer elements on an array, focused at a particular depth and direction. The acoustic wavefront formed by the superposition of the transmitted pulses propagates along the selected direction and upon backscattering from structures contained within the region of interest, propagates back towards the transducer array (refer to FIG. 1). These echos received from different transducer elements are subsequently amplified and combined using delay, phase, and apodization in such a manner as to provide a dynamic receive focus which changes as a function of time/depth along the transmitted wavefront direction. The combined signal is then log detected and further processed prior to being stored. This process is repeated many times as the transmit and receive directions are changed in such a way as to sweep through the region of interest, i.e., steered, translated, or both. Upon collecting the desired number of line acquisitions, this acoustic data is then scan converted for display to form the resulting ultrasound image. The rate at which these images are formed and displayed is referred to as the frame rate.

For an ultrasound imaging system to produce high quality images, the region of interest must be properly sampled acoustically, both in the range and azimuth (lateral) dimensions in order to prevent aliasing artifacts, which can arise in all sampled systems. In the range dimension, the Nyquist sampling theorem requires that an adequate number of samples in range be acquired based upon the combined round-trip transmit/receive pulse bandwidth. In the azimuth, or lateral, dimension, the Nyquist sampling theorem requires that 1) the region of interest be laterally insonified by a sufficient number of transmit beams and 2) an adequate number of combined round-trip transmit/receive beams laterally sample the region of interest. Stated another way, the Nyquist sampling theorem imposes a transmit acquisition lateral sampling criteria, as well as a round-trip transmit/receive lateral sampling criteria. The Nyquist transmit beam spacing $\Delta x_{xmt}$ is dependent upon the transmit aperture size $A_{xmt}$, focusing location $r_{xmt}$, and the carrier wavelength of the acoustic radiation $\lambda_0$. It is given by $$\Delta x_{xmt} = \lambda_0 F_{xmt} \quad (1)$$

where the transmit F-number $F_{xmt} = r_{xmt}/A_{xmt}$. The Nyquist round-trip beam spacing $\Delta x$ is dependent upon both transmit and receive F-numbers $F_{xmt}$ and $F_{rcv}$ respectively. It is given by $$\Delta x = \lambda_0 \frac{F_{xmt} F_{rcv}}{\sqrt{F_{xmt}^2 + F_{rcv}^2}} = \frac{\Delta x_{xmt} \Delta x_{rcv}}{\sqrt{\Delta x_{xmt}^2 + \Delta x_{rcv}^2}} \quad (2)$$

where $F_{rcv} = r_{rcv}/A_{rcv}$ for focusing location $r_{rcv}$ and $\Delta x_{rcv} = \lambda_0 F_{rcv}$. Note that when the receive F-number is much lower than the transmit F-number, the Nyquist round-trip beam spacing $\Delta x$ is dominated by the receive beam characteristics. This is the direct result of the round-trip transmit/receive beampattern $S(\omega,x,r)$ being equal to the multiplication of the individual transmit and receive beampatterns $S_{xmt}(\omega,x,r,r_{xmt})$ and $S_{rcv}(\omega,x,r)$ respectively, at a particular frequency f and range r, and is given by $$s(t, x, r) = \frac{1}{2\pi} \int S(\omega, x, r) e^{j\omega t} d\omega \quad (3)$$

$$S(\omega, x, r) = S_{xmt}(\omega, x, r, r_{xmt}) S_{rcv}(\omega, x, r)$$

$$s_{xmt}(t, x, r, r_{xmt}) = \frac{1}{2\pi} \int S_{xmt}(\omega, x, r, r_{xmt}) e^{j\omega t} d\omega$$

$$s_{rcv}(t, x, r) = \frac{1}{2\pi} \int S_{rcv}(\omega, x, r) e^{j\omega t} d\omega$$

where x is the lateral spatial coordinate, t is the time coordinate, $\omega = 2\pi f$, and the transmit, receive, and round-trip point spread functions (PSF) are the inverse Fourier transforms of their respective beampatterns. If the receive beam is much narrower than the transmit beam, then the receive beam dominates the round-trip beampattern. FIG. 2 depicts the situation where the receive beam F-number is substantially lower than the transmit F-number and as such, the receive beam, which is typically dynamically focused, i.e., the aperture size and focal point are increased as a function of time/range so as to maintain constant lateral resolution $\Delta x_{rcv}$, dominates the round-trip beam pattern. The transmit beam is generally focused at a user specified depth. Note the reduction in the round-trip sidelobe clutter energy outside of the round-trip beampattern's mainlobe at the transmit focus location, as compared to away from the transmit focus location. This is due to the multiplicative influence of the transmit beam on the receive beam. The transmit beam can have a more significant influence on the receive beam if lower transmit F-numbers are employed. However, since the transmit beam is not dynamically focused for all depths, the round-trip beampattern will display much better lateral resolution at the transmit focus location compared to away from the transmit focus location. For example, if $F_{xmt} F_{rcv}$, $\Delta x = \Delta x_{rcv}/\sqrt{2}$ at the transmit focus location, and $\Delta x = \Delta x_{rcv}$ away from the transmit focus location—a 41% degradation in lateral resolution, as well as increased sidelobe clutter. This leads to lateral image non-uniformity, which is undesirable for high quality ultrasound imaging.

Conventional ultrasound imaging systems which form a single receive beam for each transmit beam as depicted in FIG. 2, necessarily couple the Nyquist transmit beam spacing $\Delta x_{xmt}$ to the Nyquist round-trip beam spacing $\Delta x$. Instead of having to fire a minimum of $L/\Delta x_{xmt}$ transmit beams to adequately insonify the region of interest, the single beam conventional system fires $L/\Delta x$ transmit beams to cover the region of interest, where L is the lateral extent of the region of interest to be imaged. Using (1) and (2), the potential acoustic acquisition rate is reduced by the factor $$\eta = \sqrt{1 + \frac{F_{xmt}^2}{F_{rcv}^2}} = \sqrt{1 + \frac{\Delta x_{xmt}^2}{\Delta x_{rcv}^2}} \quad (4)$$

Using a typical single focus example of $F_{xmt}=2.5$ and $F_{rcv}=1.0$, the reduction in the potential acoustic acquisition rate using (4) is ~2.7. Almost three times as many transmit beams are being fired than required by Nyquist sampling requirements.

If the transmit and receive F-numbers are made equal, i.e., $F_{xmt}=F_{rcv}=1.0$, then the reduction in potential frame rate using (4) is ~1.4, which is not as dramatic as when the receive F-number is much lower than the transmit F-number; however, an additional problem is introduced, namely the limited depth of field of the transmit beam. While the receive beam is dynamically focused, the transmit beam is focused only at a single depth. The range r over which the transmit beam can be considered "in focus" is given by the depth of field expression $$R_{DOF}^{xmt} \sim \beta \lambda F_{xmt}^2, \quad 4 \leq \beta \leq 8 \quad (5)$$

$$r_{xmt} - \frac{R_{DOF}^{xmt}}{2} \leq r \leq r_{xmt} + \frac{R_{DOF}^{xmt}}{2}$$

where the choice of β depends upon what phase error is assumed at the end elements of the transmit aperture in the depth of field (DOF) derivation. Note the DOF dependence on the square of the transmit F-number. As the transmit F-number decreases, the transmit beam's lateral resolution increases linearly as given by (1); however, the range over which the transmit beam will be in focus, and have influence on the round-trip lateral resolution given by (2), decreases quadratically. This introduces image lateral non-uniformity and higher clutter away from the transmit focus and is undesirable in high quality ultrasound images. The conventional approach to mitigate this behavior is to transmit multiple times along each transmit beam, changing the transmit focus location $r_{xmt}$ on each firing and performing a conventional receive beam formation on each. The resulting multiple round-trip signals are then typically combined following the detection process, with the DOF image region around each transmit focus $r_{xmt}$ being retained, with the rest discarded. Thus, each detected line is the composite of multiple lines, each having a different transmit focus. The number of transmit firings along the same transmit beam direction that are required is dependent upon the desired transmit F-number to be supported, and the display range of the region of interest, with the number of transmit firings going up as the square of the transmit F-number reduction. This produces a significant loss in acoustic acquisition rate due to the multiple transmit firings along the same line.

BRIEF SUMMARY OF THE INVENTION

The reduction in potential acoustic acquisition rate, and ultimately frame rate, due to lateral sampling requirements, increased transmit resolution, and reduced round-trip sidelobe clutter, has led to many techniques being developed which seek to provide a true dynamic transmit focus and provide a better performance/frame rate tradeoff. The techniques developed generally fall into several classes, namely,
I. Composite,
II. Multiple beams,
III. Transmit sub-apertures,
IV. Element dependent transmit waveform generation/receive filtering, and
V. Deconvolution I. Composite techniques seek to approximate a dynamic focused transmit beam by compositing multiple transmit beams of different foci together along the same direction, either fired sequentially in time as discussed above, or simultaneous in time through linear superposition. If fired sequentially in time, the compositing of transmit beams of different foci can be performed following detection by simply discarding receive data beyond the transmit depth of field and stitching together the remaining detected receive data, which is the conventional sequential transmit approach. Or the compositing can be performed using pre-detected, i.e., coherent, receive data and combined using a weighted superposition of the coherent receive data from the multiple transmit firings. See Synthetic Dynamic Transmit Focus, Brent Robinson & Cliff Cooley, 2000 IEEE Ultrasonics Symposium, or Synthetic Transmit Focusing for Ultrasound Imaging, Bruno Haider, 2000 IEEE Ultrasonics Symposium. Compositing the transmit beams of different foci sequentially in time is not very efficient since progressively less and less information from each component transmit firing is being retained, while the number of transmit firings increases, decreasing the frame rate accordingly. Another technique composites the transmit beams of different foci simultaneous in time by linearly superimposing each transmit channel's apodized and delayed transmit waveforms together, i.e., compound focusing. See U.S. Pat. No. 5,581,517. While the multiple transmit firings in time and the commensurate decrease in frame rate are avoided, it requires a linear transmitter (which is generally more costly and power inefficient), round-trip sidelobe clutter is increased around each foci compared to a single transmit foci due to the simultaneous transmit beam's acoustic interference (which limits how close the compound transmit foci can be), and the technique does not address the reduction in potential frame rate due to transmit lateral sampling issues. A simpler, older technique simply used a transmit delay profile which was a composite of multiple transmit delay profiles each focused at different depths. The outer transmit channel's delay was dominated by the deeper transmit foci, and the inner transmit channel's delay was dominated by the shallower transmit foci. However this technique, while not reducing the frame rate, improves transmit beamformation performance away from the focus, i.e., round-trip sidelobe clutter, at the expense of beamformation performance at the focus, i.e., poorer resolution, and it still does not address the reduction in potential frame rate due to transmit lateral sampling issues.

II. Multiple beam techniques, either transmit, receive, or both, seek to improve frame by reducing the number of transmit firings it takes to laterally sample the region of interest. In the case of multiple simultaneous transmit beams, along with receive beams aligned along each transmit beam, less time is taken to sweep the region of interest to form the image for a given receive line density and thus, higher frame rate is achieved. However, the interference between the simultaneous transmit beams leads to increased acoustic clutter and degrades image quality. Using multiple receive beams formed from the same transmit beam can also improve frame rates since less time is required to sweep the region of interest for a given receive line density. However, receive beams which are spatially displaced from the transmit beam center can lead to image distortion, more so around the transmit focus, higher acoustic clutter, and results in spatial variance which is undesirable for high quality imaging. A way to mitigate this distortion was described in U.S. Pat. No. 6,016, 285, using two receive beams from each transmit firing and coherently (pre-detection) combining receive beams from two neighboring transmit firings, along with combining receive beams from the same firing as a way to re-center the receive beams along transmit firings. While eliminating geometric distortion, line-to-line gain variations are introduced, which if not removed through spatial filtering (which reduces lateral resolution) lead to imaging artifacts. A multiple beam approach, Parallel Beamforming using Synthetic Transmit Beams by T. Hergum, T. Bjastad, and H. Torp, 2004 IEEE International Ultrasonics, Ferroelectrics, and Frequency Control Joint 50$^{th}$ Anniversary Conference, pages 1401-1404, uses a weighted sum of multiple coherent receive beams from different transmit beams, forming an interpolated, or synthesized transmit beam, aligned along each receive beam. This addresses the lateral spatial sampling component of frame rate reduction, however dynamic transmit focusing is not addressed. Therefore, use of multiple beams partially addresses the lateral spatial sampling component of frame rate reduction; however, these classes of techniques have not addressed the transmit beam focusing aspect and as such, if increased transmit resolution is desired, multiple beams combined with some class of compositing is required, with the advantages and disadvantages described previously.

III. Transmit sub-aperture techniques seek to improve frame rates by trying to eliminate the process of compositing, or sequential transmit focusing, altogether by creating a dynamic transmit focus, analogous to dynamic receive focusing. The difficulty is that once the transmit wavefront is launched and propagation/diffraction begins, its characteristics cannot be directly altered. However, the effective transmit focus can be altered after the fact during receive processing by breaking up the transmit aperture into several, or many, sub-apertures (in the limit, each transducer element is fired separately) where each sub-aperture is fired sequentially in time. See Multi-Element Synthetic Transmit Aperture Imaging using Temporal Encoding by K. L. Gammelmark and J. A. Jensen, 2002 SPIE Medical Imaging Meeting, Ultrasonic Imaging and Signal Processing, 2002; pages 1-13. On receive, the echoes from each sub-aperture firing can be delayed, phased, apodized, and summed prior to, or after, receive beam formation, varying the delay, phase, and apodization values with range, to form a dynamic transmit focus. This has several limitations/complexities—first, it requires linearity in the transmit-receive processing path. While this is true for fundamental imaging, it is not strictly true for 2$^{nd}$ harmonic and higher order non-linear imaging modes. For example, in 2$^{nd}$ harmonic imaging, the transmit beam becomes essentially "squared" during the transmit propagation process, effectively reducing sidelobes and clutter in the transmit beam. The subsequent squaring that will occur during the propagation/diffraction of each transmit sub-aperture and summing on receive will not be equivalent to transmitting the entire original transmit aperture, which is the sum of the transmit sub-apertures, and squaring the result, i.e., $$\sum_{i=1}^{N_{sub}} \{G[z_i(n)]\}^2 \neq \left\{G\left[\sum_{i=1}^{N_{sub}} z_i(n)\right]\right\}^2 \quad (6)$$

$$\therefore \sum_{i=1}^{N_{sub}} \{G[z_i(n)]\}^2 \neq \left\{\sum_{i=1}^{N_{sub}} G[z_i(n)]\right\}^2$$

where n is the transmit element, $N_{sub}$ is the number of transmit sub-apertures, $z_i(n)$ represents the apodized, phased, and delayed transmit aperture function, and G is the linear propagation/diffraction operator. In other words, the sum of the squares is not equal to the square of the sums. Also, the signal-to-noise ratio (SNR), already a problem in non-linear imaging modes, will be an even greater problem using transmit sub-apertures due to the sum of the squares being less than the square of the sums. More importantly, to the extent these techniques seek to break up the transmit aperture into smaller and smaller sub-apertures, thus improving the ability to form an effective dynamic focused transmit beam, the broader and less focused each sub-aperture's individual transmit beampattern becomes, approaching that of a point source as the sub-aperture shrinks to a single element, which will have a fairly uniform amplitude distribution. Any non-linear imaging mode which reduces transmit beam sidelobe clutter through squaring, or higher order non-linearity, will no longer be as effective, i.e., squaring a uniform beam produces a uniform beam. Attempts to improve the SNR situation by transmitting on multiple elements, delayed and phased in such a way as to create point source wavefront, analogous to a single element, does increase the transmitted signal level; however, the transmit beampattern is still fairly uniform and as such, it will not see much improvement in sidelobe clutter from non-linear propagation/diffraction. Motion will be an issue in both fundamental and non-linear imaging modes since to form the entire desired transmit aperture, many firings may be required, i.e., 128, etc., which will require a fair amount of time. For example, assuming a carrier frequency of 3.5 MHz, a depth of 240 mm with an assumed sound speed of 1540 m/s, the round-trip propagation time is 311 µsec, which for 128 elements/firings is 40 msec. This is quite a long time for phase coherency to be maintained across the elements to a fraction of the 3.5 MHz wavelength, which is 0.44 mm. Motion during that time will introduce transmit beamformation delay/phase errors due to the many firings it takes to construct the effective transmit beam, which will degrade the quality of the effective transmit beam characteristics and introduce increased acoustic clutter and other motion artifacts. Lastly, depending upon how many transmit sub-apertures are employed, the processing requirements can be quite high, which can be even higher if motion compensation techniques are considered, making some of these techniques impractical for real-time imaging given the current state of the art technology.

IV. Techniques that use element dependent transmit waveform generation, possibly combined with receive filtering, seek to employ different transmit waveforms on each element in such a way that during propagation and diffraction, the individual waveforms combine which, when filtered on receive, an effective dynamic focused transmit beam is formed. U.S. Pat. No. 6,108,273 describes starting with a traditional short pulse at the center of the transmit aperture, whose higher spectral frequency components are progressively advanced in time compared to the lower frequency components, as the transmit element location approaches either end of the transmit aperture. This produces a chirp-like waveform of increasing length away from the transmit aperture center. On receive, a bandpass filter is employed whose center frequency is decreased with depth. The transmitted pulse's higher frequency components that are selectively passed by the depth dependent receive bandpass filter have diffracted from a transmit delay arc of higher curvature, which effectively focuses the transmit wavefront at shallower depths. The transmitted pulse's lower frequency components that are selectively passed by the depth dependent receive bandpass filter have diffracted from a transmit delay arc of lower curvature, which effectively focuses the transmit wavefront at deeper depths. This approximates a dynamically focused transmit beam. The limitations of this approach is that the potential round-trip pulse bandwidth and hence, axial resolution, is compromised at the expense of the dynamic transmit focusing effect. In addition, this technique alone does not address the lateral spatial sampling component of frame rate reduction, although some of the other techniques outlined could be used in conjunction with this technique.

V. Techniques that use a deconvolution approach to improve the transmit focusing characteristics also have various limitations. For example, Retrospective Dynamic Transmit Focusing by S. Freeman, Pai-Chi Li, and M. O'Donnell, Ultrasonic Imaging 17, pages 173-196, (1995), used a single receive beam system along with a spatial filter of a finite number of taps, operating across receive beams. The design of the spatial filter was designed with the intent to deconvolve out the effects of the defocused transmit beam from the round-trip point spread function. As such, this approach will be limited by the receive beam's influence on the round-trip point spread function, reducing the extent to which the transmit focusing characteristics can be improved. In addition, it does not address the lateral spatial sampling component of frame rate reduction.

The present invention seeks to provide high quality imaging using a minimum of transmit firings by decoupling the Nyquist transmit and round-trip spatial sampling requirements, and at the same time maintaining a continuous transmit focus throughout the region of interest, which reduces or eliminates the need for transmit focus compositing, i.e., sequential transmit focus, both of which dramatically improve the acoustic acquisition rate. Reduction of the number of transmit firings becomes especially important for ultrasound systems which are battery powered in order to conserve energy and reduce power consumption. Elimination of transmit focus user controls is also a desirable feature, especially for portable ultrasound systems given their compact user interface. The invention works in linear or non-linear imaging modes, works with standard 1-D and 2-D transducer arrays, can be extended to three spatial dimensions, i.e., 3-D imaging, is compatible with all scan formats, and is robust in presence of motion.

An aspect of the present invention is directed to an ultrasound imaging method for achieving transmit and receive focusing at every echo location within a region of interest. The method comprises providing a probe that includes one or more transducer elements for transmitting and receiving ultrasound waves; generating a sequence of spatially distinct transmit beams which differ in one or more of origin and angle; determining a transmit beam spacing substantially based upon a combination of actual and desired transmit beam characteristics, thereby achieving a faster echo acquisition rate compared to a transmit beam spacing based upon round-trip transmit-receive beam sampling requirements; storing coherent receive echo data, from two or more transmit beams of the spatially distinct transmit beams; combining coherent receive echo data from at least two or more transmit beams to achieve a substantially spatially invariant synthesized transmit focus at each echo location, i.e., to achieve transmit synthesis; and combining coherent receive echo data from each transmit firing to achieve dynamic receive focusing at each echo location.

In some embodiments, the probe is a 1-D, 2-D array with varying degrees of elevation beamforming control, including aperture, delay, and phase, or a general 2-D scanning array, or a sparse 1-D or 2-D array. The spatially distinct transmit beams are generated electronically, mechanically, or any combination thereof; to scan a 2-D plane or 3-D volume. Coherent receive echo data is receive channel data from different transducer elements. Combining coherent receive echo data from each transmit firing to achieve dynamic receive focusing is performed prior to combining coherent receive echo data from at least two or more transmit beams to achieve transmit synthesis. Combining coherent receive echo data from each transmit firing to achieve dynamic receive focusing is performed prior to storing coherent receive echo data. Alternatively, combining coherent receive echo data from each transmit firing to achieve dynamic receive focusing is performed subsequent to combining coherent receive echo data from at least two or more transmit beams to achieve transmit synthesis. In other embodiments, combining coherent receive echo data from each transmit firing to achieve dynamic receive focusing and combining coherent receive echo data from at least two or more transmit beams to achieve transmit synthesis are performed in combination.

In specific embodiments, combining coherent receive echo data from each transmit firing to achieve dynamic receive focusing and combining coherent receive echo data from at least two or more transmit beams to achieve transmit synthesis are performed at arbitrary echo locations, i.e., area/volume formation, or along multiple ray-like paths, i.e., multiple receive beamformation. One or more non-linear components of the transmitted ultrasound waves are included in the steps of storing coherent receive echo data, combining coherent receive echo data from each transmit firing to achieve dynamic receive focusing, and combining coherent receive echo data from at least two or more transmit beams to achieve transmit synthesis. The method may further comprise forming an image with an imaging mode that includes one or more of B, color Doppler (velocity, power), M, spectral Doppler (PW), with or without using contrast agents. Velocity imaging modes including color velocity and spectral Doppler (PW) are achieved using motion compensation in combining coherent receive echo data from at least two or more transmit beams to achieve transmit synthesis. The spectral Doppler (PW) mode involves processing one or more sample volumes along a synthesized transmit beam obtained by the transmit synthesis.

In some embodiments, combining coherent receive echo data from at least two or more transmit beams to achieve transmit synthesis includes combining using one or more of delay, phase, amplitude, and convolution. Combining coherent receive echo data from at least two or more transmit beams to achieve transmit synthesis may be responsive to echo location, as well as to the spatial and temporal characteristics of the actual and/or desired transmit beam characteristics, which may include one or more non-linear components of the transmitted ultrasound waves. The spatially distinct transmit beams may differ in one or more of delay, phase, apodization, amplitude, frequency, or coding. The spatially distinct transmit beams may have a single focus at a predetermined range, with an F-number ranging from 0.5 to 10. Two or more of the spatially distinct transmit beams are fired simultaneously, or with a time gap less than a round-trip propagation time, for faster echo acquisition.

Another aspect of the invention is directed to an ultrasound imaging system for achieving transmit and receive focusing at every echo location within a region of interest. The system comprises a probe that includes one or more transducer elements for transmitting and receiving ultrasound waves; and a processor. The processor generates a sequence of spatially distinct transmit beams which differ in one or more of origin and angle; determines a transmit beam spacing substantially based upon a combination of actual and desired transmit beam characteristics, thereby achieving a faster echo acquisition rate compared to a transmit beam spacing based upon round-trip transmit-receive beam sampling requirements; stores coherent receive echo data, from two or more transmit beams of the spatially distinct transmit beams; combines coherent receive echo data from at least two or more transmit beams to achieve a substantially spatially invariant synthesized transmit focus at each echo location, i.e., to achieve transmit synthesis; and combines coherent receive echo data from each transmit firing to achieve dynamic receive focusing at each echo location.

DETAILED DESCRIPTION OF THE INVENTION

The present invention seeks to provide high quality imaging using a minimum of transmit firings by decoupling the Nyquist transmit and round-trip spatial sampling requirements, and at the same time maintaining a continuous transmit focus throughout the region of interest, which reduces or eliminates the need for transmit focus compositing, i.e., sequential transmit focus, both of which dramatically improve the acoustic acquisition rate. Reduction of the number of transmit firings becomes especially important for ultrasound systems which are battery powered in order to conserve energy and reduce power consumption. Elimination of transmit focus user controls is also a desirable feature, especially for portable ultrasound systems given their compact user interface. The invention works in linear or non-linear imaging modes, works with standard 1-D and 2-D transducer arrays, can be extended to three spatial dimensions, i.e., 3-D imaging, is compatible with all scan formats, and is robust in presence of motion.

Figure 1:
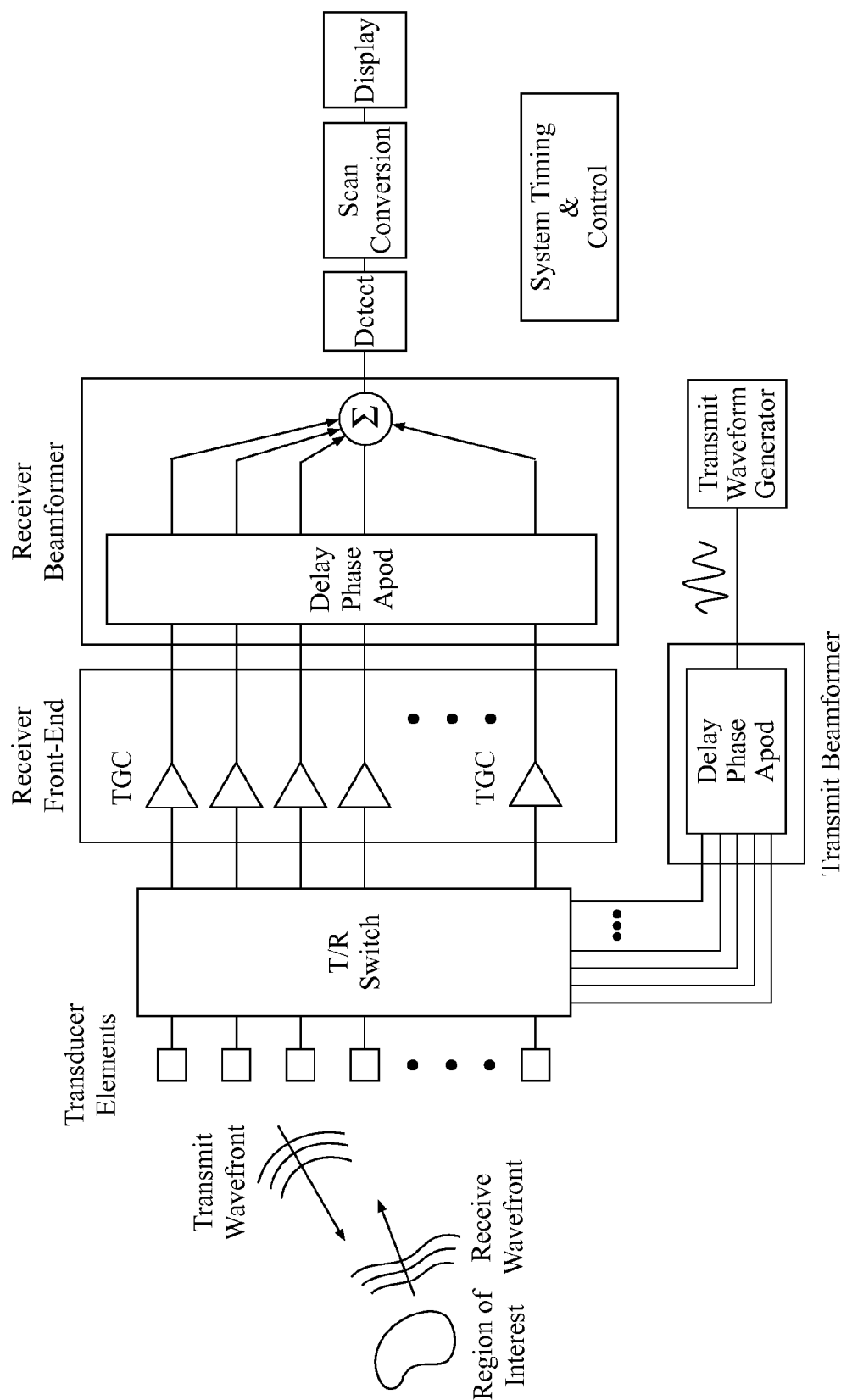
FIG. 1 is a block diagram of the system architecture of a conventional ultrasound imaging system.
Figure 2:
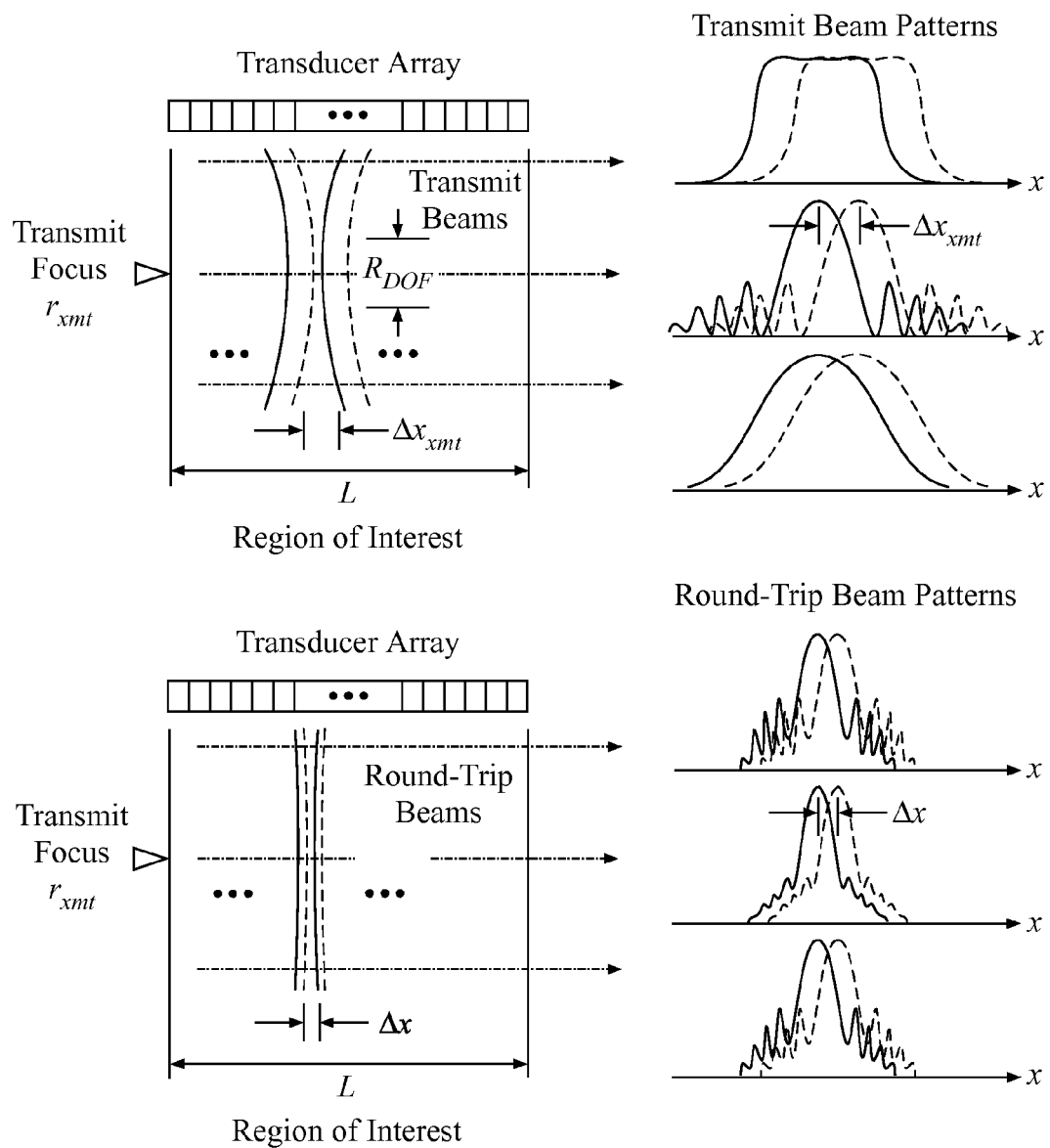
FIG. 2 shows transmit and round-trip beam patterns, as well as transmit and round-trip lateral sampling requirements, for conventional ultrasound imaging systems which form a single receive beam for each transmit beam.
Figure 3:
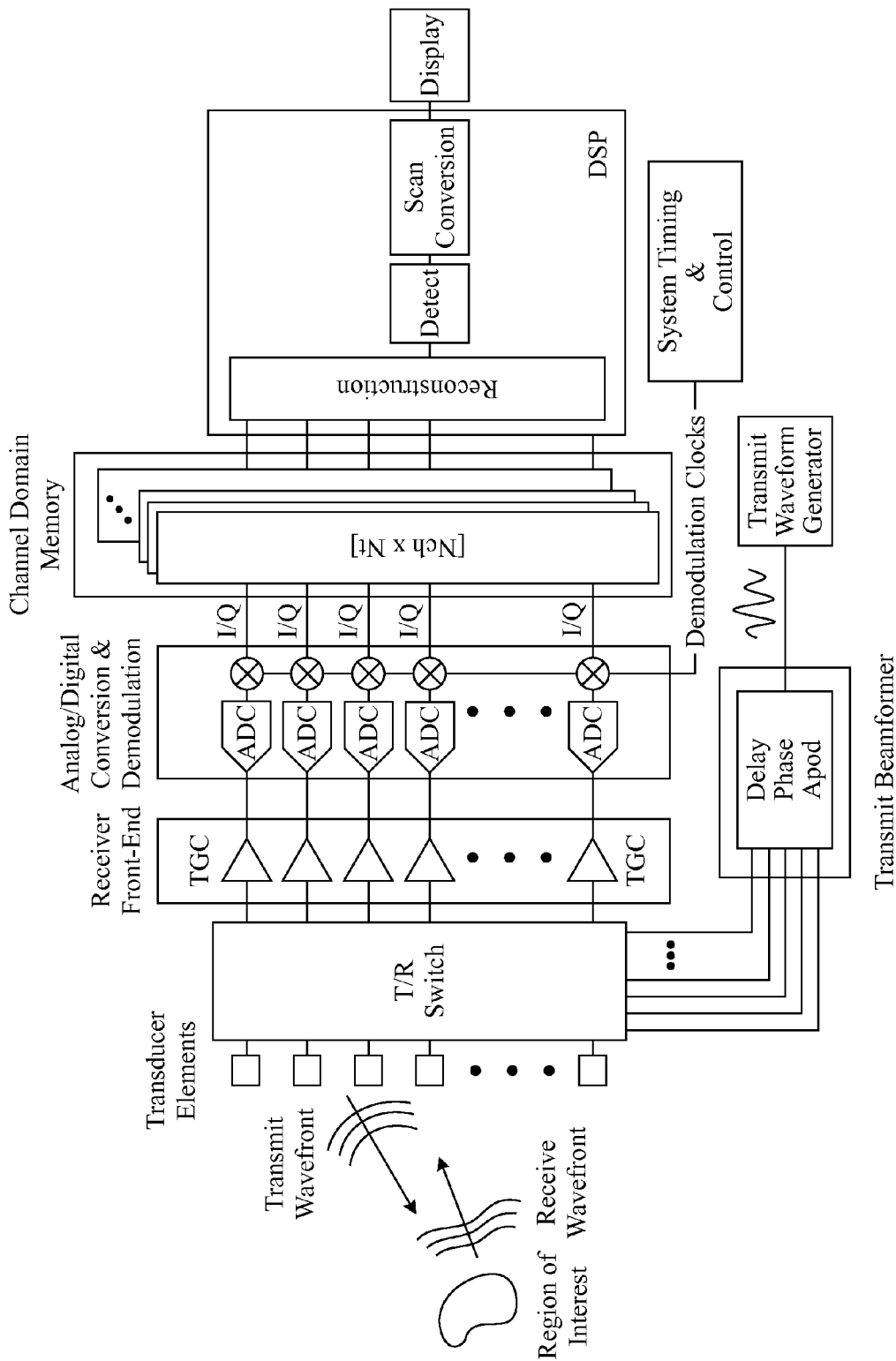
FIG. 3 is a block diagram of the system architecture of an ultrasound imaging system according to an embodiment of the present invention.

FIG. 3 shows a block diagram of the system architecture according to an embodiment of the present invention. However, this is but a representative example and many other system architectures can be used. Referring to FIG. 3, following receive front-end TGC, analog-to-digital conversion and demodulation from RF to baseband is performed. The resulting in-phase and quadrature, i.e., I/Q, data is then stored into a random access channel domain memory. The memory can be SDRAM, MRAM, or any other suitable memory device. Equivalently, magnitude and phase data could be stored. The channel domain memory holds Nt time samples for all Nch system channels, for an arbitrary number of transmit firings, i.e., the number of transmit firings required to insonify the entire region of interest—a frame, or more. Next, the channel domain I/Q data is read by the digital signal processor (DSP) and employing software algorithms, the DSP performs receive reconstruction, detection, and scan conversion for display. Alternatively, the DSP may consist of a single DSP or multiple DSP's, or a combination of programmable logic, i.e., FPGA's, and DSP's. The receive reconstruction process is analogous to receive beamformation; however, it is more general and, in conjunction with the random access channel domain memory and DSP/software programmable architecture, provides arbitrary spatial sampling, allowing it to take advantage of spatially dependent sampling requirements and reduce computation time.

Figure 4:
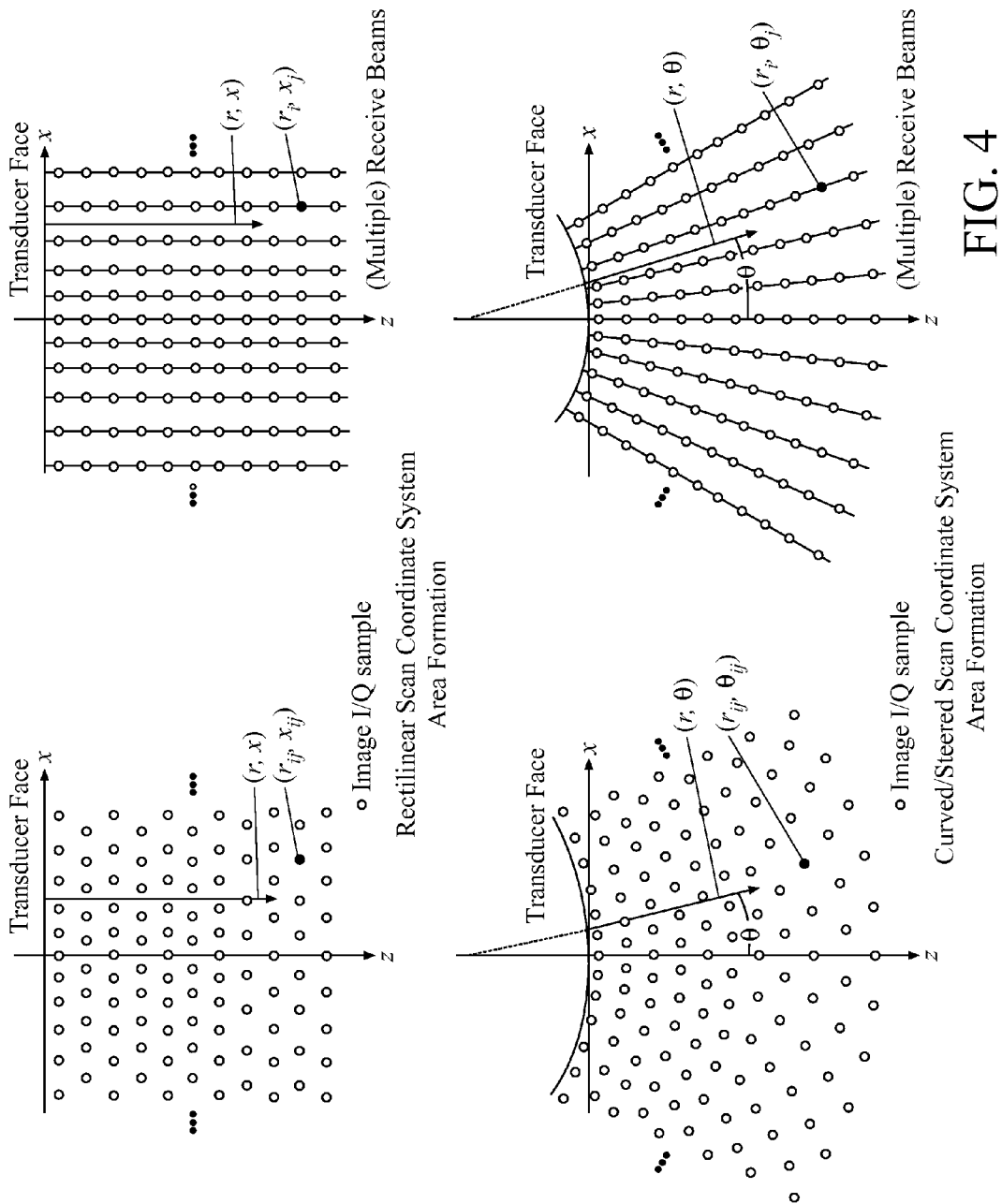
FIG. 4 shows examples of area formation for a rectilinear scan coordinate system and a curved/steered scan coordinate system.

Reconstruction represents the transformation of channel data into pre-detection image data over an area or volume, from the insonification by a focused, broad, or defocused transmit beam, defined as a transmit zone. The area is defined by a collection of range and azimuth coordinates, where the azimuth coordinate is defined by a suitable lateral coordinate, i.e., horizontal position x, steering angle $\theta$, etc. This is shown in FIG. 4 which depicts several representative examples. The transducer can be planar, curved, or of some other form, and the scan geometry, i.e., transmit/receive beam origins and angles, can be arbitrary. The random access channel domain I/Q data memory allows the DSP to form an arbitrary I/Q point from any transmit firing, or zone. Alternatively, the DSP can use channel magnitude and phase data to form a magnitude and phase point. The reconstruction software algorithm in the DSP may include channel delay, phase, apodization, and summation processing as is well known in the art to form an image I/Q point, but it is not limited to this particular image formation technique and can include non-linear processing elements. In general, the collection of range and azimuth coordinates defining a reconstructed I/Q point within the area formation region, from any given transmit zone, can be described by $$r_{ij}=f_r(r;x,i,j,\ldots) \text{ or } r_{ij}=f_r(r;\theta,i,j,\ldots)$$

$$x_{ij}=f_x(r;x,i,j,\ldots) \text{ or } \theta_{ij}=f_\theta(r;\theta,i,j,\ldots) \quad (7)$$

where $f_{\{r,x,\theta\}}$ describes the functional dependence of the specified coordinate on its input parameters, (i,j) are suitable indexing parameters, and . . . indicates any other parameter dependence for the range and azimuth coordinates, i.e., transmit focus location, etc. If the collection of range and azimuth coordinates defining the reconstructed area are independent and assume a more standard dependence on the indexing parameters, i.e., $$r_i = r_0 + i \cdot \Delta r \; i = \{0, 1, \ldots N_r - 1\}$$

$$x_j = x_0 + j \cdot \Delta x \; j = \{0, 1, \ldots N_x - 1\}$$

or $$\theta_j = \theta_0 + j \cdot \Delta\theta\, j = \{0, 1, \ldots N_\theta - 1\} \quad (8)$$

then area formation reduces to standard receive beamformation, i.e., ray-like paths. In the case where more than one of these receive beams are formed simultaneously from a single transmit firing, or zone, then it is considered multiple receive beamformation, also known in the art as parallel beamformation. In three spatial dimensions, i.e., 3-D imaging, area formation becomes volume formation and can be described by a collection of suitable range, azimuth, and elevation coordinates. The examples shown in FIG. 4 can be easily extended into three spatial dimensions, i.e., if y represents the elevation coordinate, then $$r_{ijk} = f_r(r, x, y, i, j, k, \ldots)$$

$$x_{ijk} = f_x(r, x, y, i, j, k, \ldots)$$

$$y_{ijk} = f_y(r, x, y, i, j, k, \ldots) \quad (9)$$

If angular coordinates are preferred in describing the desired scan geometry, then equation (9) can be suitably modified. If the collection of range and azimuth coordinates defining the reconstructed volume are independent and assume a more standard dependence on the indexing parameters, i.e., $$r_i = r_0 + i \cdot \Delta r\, i = \{0, 1, \ldots N_r - 1\}$$

$$x_j = x_0 + j \cdot \Delta x\, j = \{0, 1, \ldots N_x - 1\}$$

$$y_k = y_0 + k \cdot \Delta y\, k = \{0, 1, \ldots N_y - 1\} \quad (10)$$

If angular coordinates are preferred in describing the desired scan geometry, then (10) can be suitably modified.

It is important to note that if the transmit and round-trip spatial sampling requirements are decoupled using the system architecture shown in FIG. 3, thereby reducing or eliminating the potential acoustic acquisition reduction factor $\eta$ given by (4), then the frame rate is essentially decoupled from the acoustic acquisition frame rate. While the acoustic acquisition rate is determined by the number of transmit firings and acoustic propagation time, the frame rate will be determined by the DSP and software algorithm's computation time required to process the acquired channel I/Q data and form image I/Q data, i.e., area formation, perform detection, scan conversion, etc., and display the image, up until the acoustic acquisition rate becomes the limiting factor. This characteristic provides the system the opportunity to produce high quality images at much higher frame rates than conventional systems, provided sufficient processing performance is utilized. Alternatively, the system could expend the additional time available performing more sophisticated image formation algorithms to further improve image quality, reduce system power consumption by maintaining the frame rate at conventional system frame rates, etc. The channel domain data memory serves as a buffer between the acoustic acquisition rate and the DSP and software algorithm processing rate.

Figure 5:
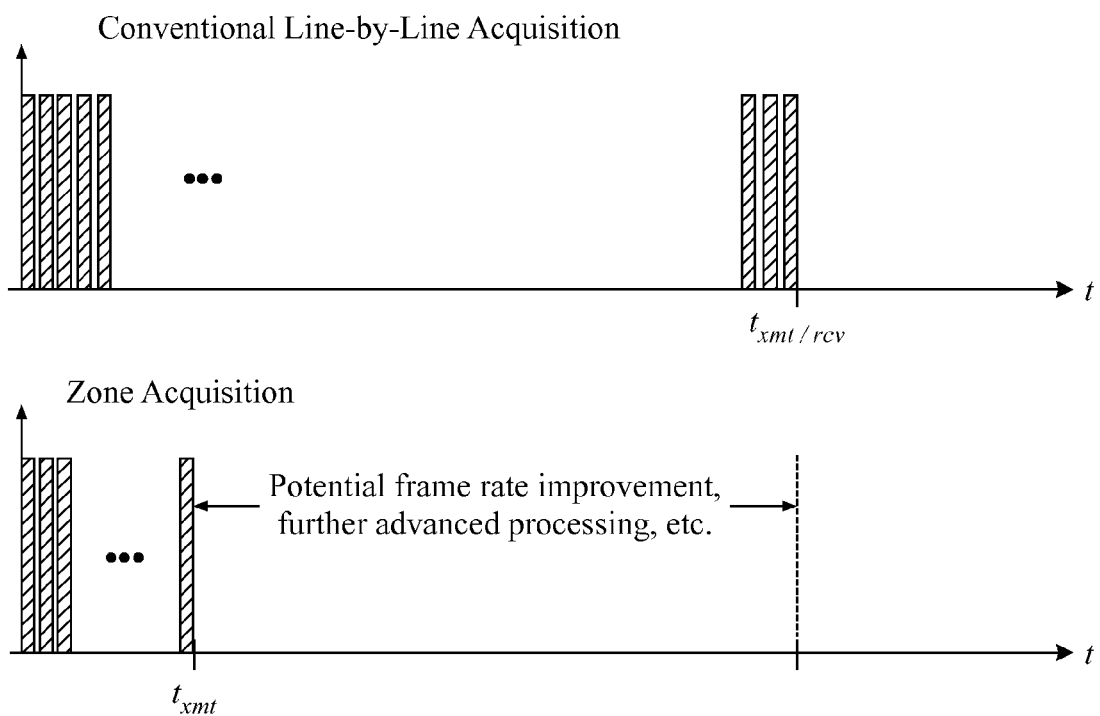
FIG. 5 shows a comparison between conventional single-beam line-by-line acoustic acquisition where the transmit and round-trip spatial sampling requirements are coupled, and zone acquisition of the present invention where the transmit and round-trip spatial sampling requirements are decoupled.

FIG. 5 shows a comparison between conventional single-beam line-by-line acoustic acquisition where the transmit and round-trip spatial sampling requirements are coupled, and zone acquisition of the present invention where the transmit and round-trip spatial sampling requirements are decoupled. Depending upon the transmit F-number, the improvement in acoustic acquisition rate compared to conventional systems can be substantial as described previously. The process by which the region of interest is insonified based upon transmit sampling requirements alone is termed zone acquisition, from which a relatively large image I/Q area can be reconstructed from channel I/Q data such that round-trip Nyquist spatial sampling requirements are met or exceeded. To the extent that area formation reduces to the special case of multiple receive beamforming, then the receive beam density must meet or exceed Nyquist round-trip sampling requirements.

The zone acquisition process can be easily extended to three dimensions to yield even larger improvements, where the large number of transmit firings typically required by conventional systems results in very low frame rates. The zone acquisition process has advantages in other applications. For example, in contrast agent imaging where micro-bubbles are injected into the body and imaged with ultrasound, either at essentially the same insonification frequency or suitable harmonic, reducing the number of transmit firings and increasing the lateral spacing of the transmit beams results in less bubble destruction where minimum or no bubble destruction is desired.

The procedure to decouple transmit and round-trip spatial sampling requirements, as well as provide a continuous transmit focus, is now described for an embodiment of the present invention. The motivation for this technique is based upon the following line of reasoning. A conventional fixed-focused transmit beam produces high quality images around the focus, and works well in harmonic imaging modes, etc., however lateral resolution and uniformity degrade away from the focus. Rather than reinventing the transmit beam, i.e., decomposing the transmit aperture into many pieces, only to sum the resulting component beam responses back up on receive as outlined in some of the other techniques, suffering the many disadvantages described, the present embodiment simply corrects the transmit beam away from the focus as needed. This can be accomplished using the following insight. Consider a single receive element on a transducer array receiving the backscattered signal from the transmit pulse wavefront impinging on a point scatterer in the region of interest. As the transmit beam is swept through the region of interest, the received backscattered signal from the point scatterer, on a given receive element, will sample the transmit beam from unique spatial locations. In principle, if the transmit beam can be adequately sampled in time as well as in space, then a spatial-temporal filter can be designed that can transform the actual transmit beam into that of another transmit beam of differing spatial and temporal characteristics, provided that the transmit beam's spatial and temporal characteristics are sufficiently predictable. The receive element on the transducer array provides that sampling. For example, if a point scatterer in the region of interest lies in the unfocused region of the transmit beam, i.e., at a depth shallow to the transmit focus, then the evolution of signals received on a given transducer element, as the transmit beam is swept through the region of interest, will provide a representation of the defocused transmit beam.

Figure 6:
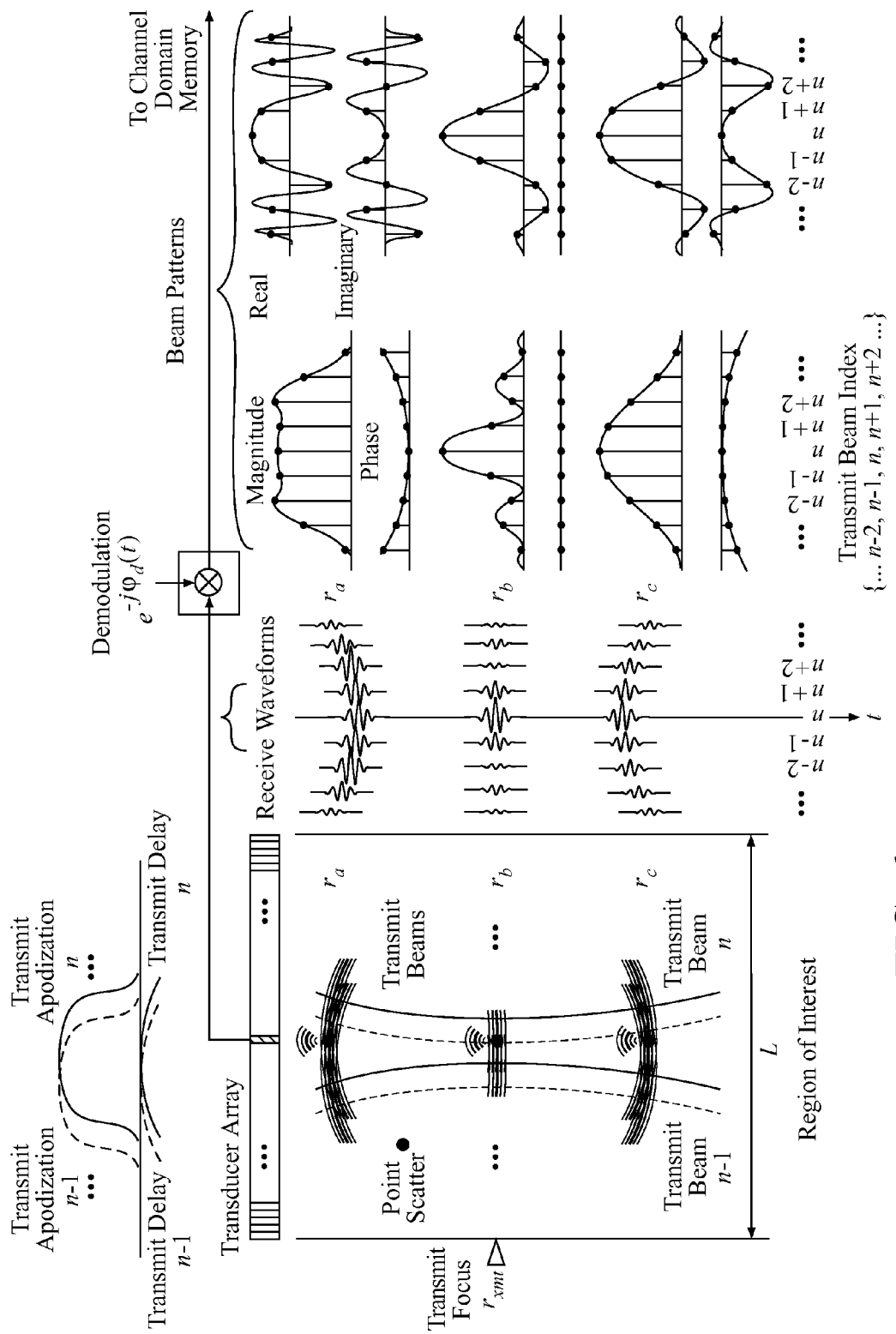
FIG. 6 illustrates transmit beam sampling for a planar transducer array employing a linear scan format according to an embodiment of the present invention.

FIG. 6 shows an example of a planar transducer array employing a linear scan format, where a single point scatterer is located at either $r=r_a$, (a depth shallow to the transmit focus), $r=r_b$ (a depth at the transmit focus), or $r=r_c$ (a depth deeper than the transmit focus), are shown. The transmit apodization and delay profiles are translated across the transducer array so as to translate the transmit beam across the region of interest. The transmit beam's pulse waveform, after having been subjected to frequency dependent attenuation, $1/r$ falloff, the transducer's receive spectral response for the element shown, as well as any other filter response in the receive signal path, produces the receive waveforms shown. The evolution of these receive waveforms as the transmit beam is translated across the region of interest are shown at times corresponding to a point scatterer depth of either $r_a$, $r_b$, or $r_c$. For a given point scatterer depth, the receive waveform is shifted in time according to how long the transmit beam's wavefront takes to propagate from the transducer face, to the point scatterer, and back to a given receive element, referenced to a suitable time origin, as the transmit beam is translated across the region of interest. For a point scatterer at $r=r_a$, the receive waveform arrives earlier at the edge of the transmit beam, and later for the center of the transmit beam due to the focusing curvature. For a point scatterer at either $r=r_b$ or $r=r_c$, the receive waveforms display the behavior shown for analogous reasons.

Now consider the demodulated receive waveforms. For a given time/range sample lying within the evolution of receive waveforms from a given point scatterer depth, plotting the magnitude and phase, or equivalently, real and imaginary, i.e., I/Q, values of the given time/range sample as the transmit beam is swept through the region of interest will result in the beam patterns shown in FIG. 6. At range locations $r=r_a$ or $r=r_c$, away from the transmit focus depth, the beam pattern is defocused and broad, displaying the classic quadratic phase error. At range location $r=r_b$, the beam pattern is focused. The real and imaginary beam pattern components display the same behavior. One skilled in the art will recognize the beam patterns away from the transmit focus as that of a chirp waveform, albeit a spatial chirp as opposed to a temporal chirp, and is the result of the transmit beam's approximately parabolic delay profile. Diffraction provides the spatial compression necessary to transform the defocused transmit beam in the near field to a focused beam at the focus location, however only at the focus location. Therefore, in order to produce a focused transmit beam for all ranges, a spatial filter is required to correct the transmit beam away from the transmit focus, correcting for diffraction effects, and perform spatial compression throughout the region of interest.

Transmit Synthesis—Spatial Diffraction Transform

The following analysis will consider several examples which are intended to illustrate the transmit synthesis technique; however, the invention is not meant to be limited by the examples provided. Note that in the analysis, continuous time is used for simplicity unless otherwise noted. Sampled time can also be used in an analogous manner.

Figure 7:
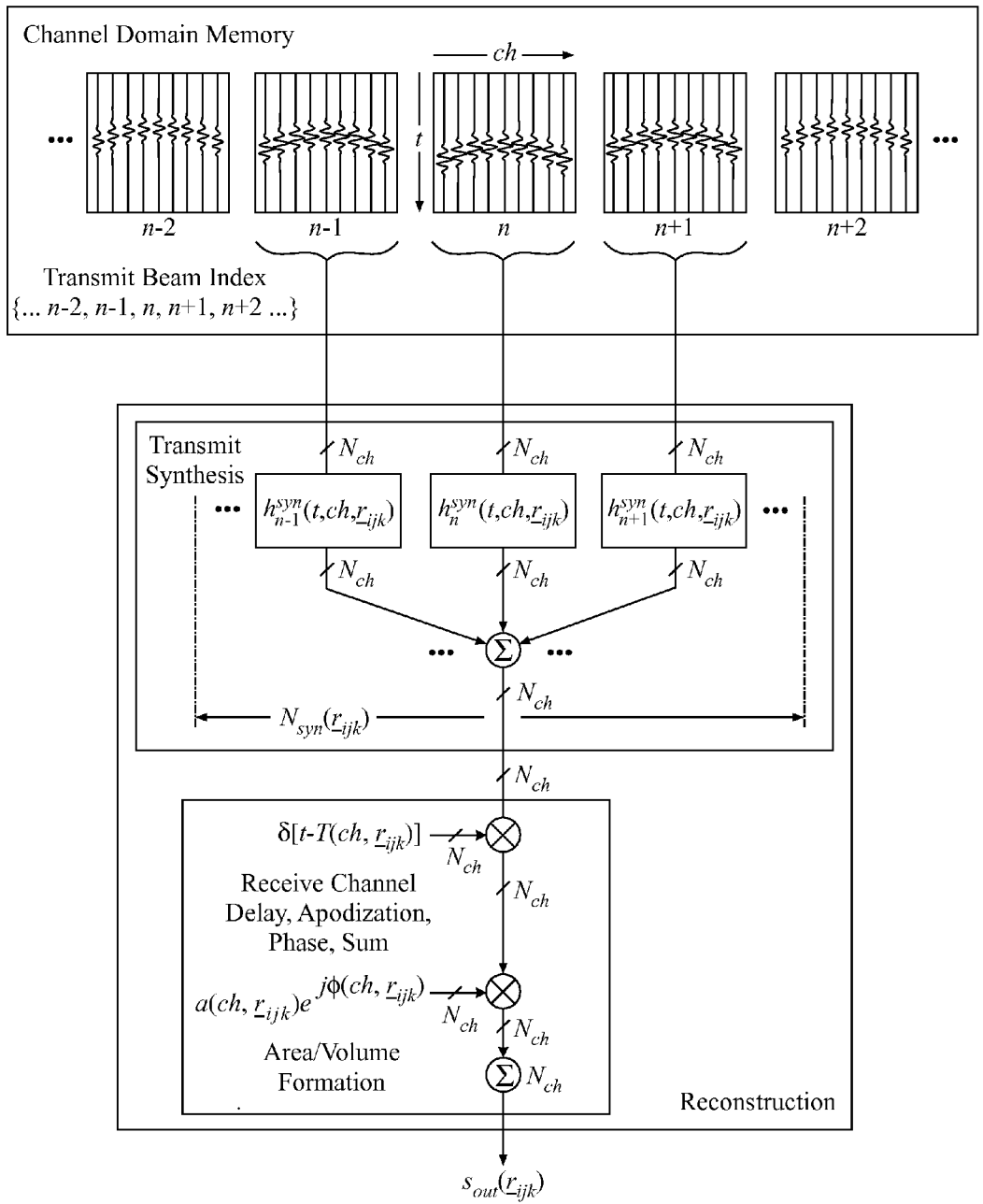
FIG. 7 shows an architecture topology of image/volume reconstruction (Image/Volume Reconstruction I) according to one embodiment of the present invention.
Figure 8:
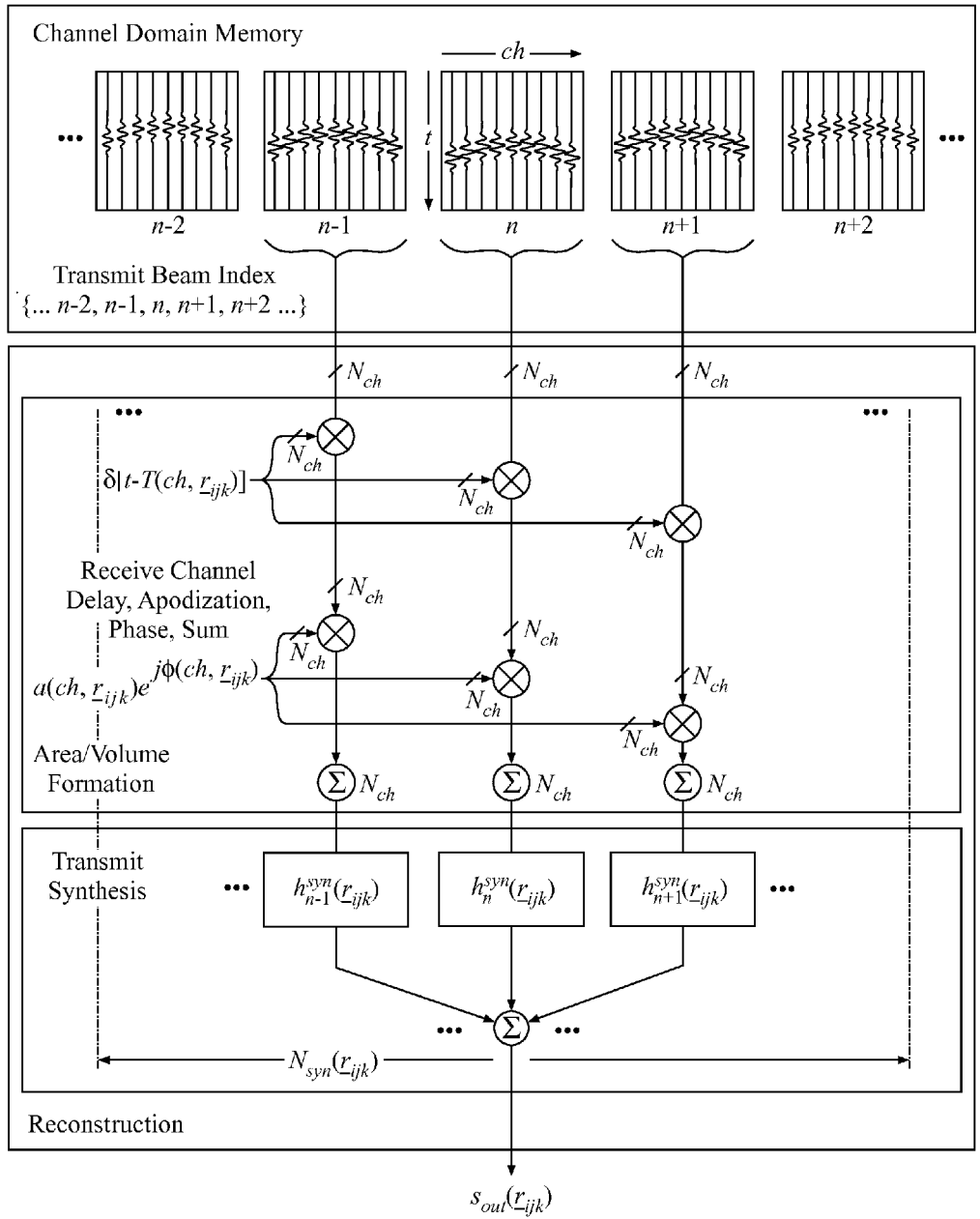
FIG. 8 shows an architecture topology of image/volume reconstruction (Image/Volume Reconstruction II) according to another embodiment of the present invention.

Consider the architecture topologies shown in FIG. 7 (Image/Volume Reconstruction I) and FIG. 8 (Image/Volume Reconstruction II). Received channel data from each transmit beam firing n is acquired and stored in channel domain memory. This channel domain data can either be received RF, demodulated RF to IF, or demodulated to baseband I/Q signals from the transducer elements, or other suitable representation. The sequence of transmit beam firings can be swept through the region of interest in an arbitrary fashion, either in two or three dimensions. The transmit beam can be swept through the region of interest either electronically, mechanically, or any combination thereof. The transmit beams from spatial location to spatial location may differ in characteristics such as amplitude, phase, delay, carrier frequency, focusing characteristics, waveforms, coding, etc. The transducer employed can be either conventional 1-D arrays, 1½-D arrays, or 2-D matrix arrays. In FIG. 7, the Transmit Synthesis block precedes the Area/Volume Formation block, whereas in FIG. 8 the Transmit Synthesis block follows the Area/Volume Formation block. In both cases, the Reconstruction block contains both Transmit Synthesis and Area/Volume Formation Blocks. The Transmit Synthesis block in FIG. 7 consists of transmit beam n, time t, channel ch, and spatial coordinate $r_{ijk}$ dependent filters $h^{syn}$ whose outputs are summed together across $N_{syn}(r_{ijk})$ transmit beam firings. This is followed by the Area/Volume Formation block, which can form an output point $s_{out}(r_{ijk})$ at location $r_{ijk}$ using time, channel, and spatially dependent delay, apodization, phase, and summing across $N_{ch}$ channels, or some other suitable algorithm. In FIG. 8, the Area/Volume Formation block operates across channel data acquired from $N_{syn}(r_{ijk})$ transmit beam firings, either applying a time, channel, and spatially dependent delay, apodization, phase, and summing across $N_{ch}$ channels, or other suitable algorithm, producing $N_{syn}(r_{ijk})$ outputs. Each of these outputs in turn are applied to the Transmit Synthesis block, consisting of $N_{syn}(r_{ijk})$ spatial coordinate $r_{ijk}$ dependent filters $h^{syn}$ whose outputs are then summed together across the $N_{syn}(r_{ijk})$ transmit beam firings to form an output point $s_{out}(r_{ijk})$ at location $r_{ijk}$. Now since the received signals on each of the transducer elements provide a representation of the transmit beam pattern over the evolution of transmit beam spatial firings, a spatial filter $h^{syn}$, whose region of support operates on either the channel signals, or area/volume formed signals, across a finite number of the sequence of transmit beam spatial firings which cover the region of interest, provides the desired spatial compression through a properly delayed, phased, weighted, and filtered superposition. Therefore, the Transmit Synthesis block which performs this filtering process can be viewed as a spatial diffraction transform since it transforms the actual transmit diffraction response into a desired transmit diffraction response, whose characteristics, both temporal and spatial, can be substantially different.

While the transmit synthesis technique will be covered in more detail, at a high level, the basic idea is the following. Consider an expression for the round-trip beampattern formed from a sequence of transmit beams whose apertures are centered at $n\Delta x$ $$S_n(\omega,x) = S_{xmt}(\omega,x-n\Delta x)S_{rcv}(\omega,x) \quad (11)$$

where $S_{xmt}$ is the transmit beampattern, $S_{rcv}$ is the receive beampattern, $\omega$ is the carrier frequency, x is the target's lateral position, and $$s_n(t,x) = \frac{1}{2\pi}\int S_n(\omega,x)P(\omega)e^{j\omega t}d\omega \quad (12)$$

where $s_n(t,x)$ is the round-trip point spread function response for pulse spectrum $P(\omega)$. Forming a linear combination of the sequence of roundtrip beampatterns, yields $$S^{syn}(\omega,x) = \sum_{n=1}^{N_{syn}} H_n(\omega)S_n(\omega,x) \quad (13)$$

$$= \sum_{n=1}^{N_{syn}} H_n(\omega)S_{xmt}(\omega,x-n\Delta x)S_{rcv}(\omega,x)$$

This can be rewritten as $$S^{syn}(\omega,x) = S^{syn}_{xmt}(\omega,x)S_{rcv}(\omega,x) \quad (14)$$

-continued $$S_{xmt}^{syn}(\omega, x) = \sum_{n=1}^{N_{syn}} H_n(\omega) S_{xmt}(\omega, x - n\Delta x)$$

$$= \sum_{n=1}^{N_{syn}} \underbrace{|H_n(\omega)| e^{j\psi_n(\omega)}}_{H_n(\omega)} S_{xmt}(\omega, x - n\Delta x)$$

where $H_n(\omega)$ can be thought of as a diffraction correction filter (complex in general, i.e., magnitude/phase, real/imaginary, etc.), the filtering operation termed diffraction transform. Thus, the operation attempts to transform, or correct, a sequence of actual transmit diffraction patterns $S_{xmt}(\omega, x-n\Delta x)$, into the desired transmit diffraction pattern $S_{xmt}^{syn}$ using $N_{syn}$ zones.

The symbols in the above equations are defined as follows:
$r_{xmt}$=transmit focus range along the transmit beam direction
$\underline{r}$=point scatterer location in 2-D/3-D space
$\underline{r}'$=transducer array receive element location in 2-D/3-D space, either electronically swept, mechanically swept, or a combination thereof
$\underline{r}_{ijk}$=image/volume point location in 2-D/3-D space respectively
$\phi(t)$=demodulation phase
$s_{xmt}(t)$=transmitted RF pulse waveform from transducer element
$\tilde{s}_{xmt}(t, \underline{r}, \ldots)$=transmit beam RF pulse wavefront at point scatterer location $\underline{r}$ due to transmit excitation $s_{xmt}(t)$, where ~ indicates that the pulses transmitted by each element on the array will interfere at the location $\underline{r}$ and therefore, the temporal response of the pulse may be altered due to transmit diffraction
$\tilde{s}_{ch}(t, \ldots)$=receive channel signal from transducer element following TGC, A/D conversion, demodulation, baseband filtering, etc. ~ indicates that the pulses received by each element on the array may have been altered by transmit diffraction
$T_{xmt}(\ldots)$=effective time delay of the transmit beam RF pulse wavefront $\tilde{s}_{xmt}(t, \underline{r}, \ldots)$ to a point scatterer located at $\underline{r}$, i.e., the propagation delay plus the differential delay arc of the transmit pulse wavefront, $\Delta T_{xmt}$, due to diffraction
$T_{rcv}(\ldots)$=time delay of the backscattered pulse from a point scatterer located at $\underline{r}$ to a transducer receive element
$T(ch, \underline{r}_{ijk})$, $\phi(ch, \underline{r}_{ijk})$, $a(ch, \underline{r}_{ijk})$=receive channel delay and phase correction, and apodization, used in area/volume formation in 2-D/3-D space
$h_{rcv}(t)$=receive filter which includes the effects of frequency dependent attenuation, 1/r falloff, element response, the transducer's one-way receive response, etc.
$h^{syn}(\ldots)$=transmit synthesis filter
$N_{syn}(\ldots)$, $\underline{N}_{syn}(\ldots)$=number/list of transmit beams in 2-D/3-D space used in transmit synthesis Example Planar 1-D Transducer, Linear Scan Format, 2-D Image Formation Consider the demodulated receive signal from a given transducer element as shown in FIG. 6. The signal $\tilde{s}_{ch}$ received by a transducer element located at $r'=x'_p$, from a point scatterer at $r=(r,x)$, insonified by the n-th transmit beam wavefront $\tilde{s}_{xmt}(t-T_{xmt},x-x_n,r,r_{xmt})$, due to a transmit excitation of $s_{xmt}(t)$, where $x_n$ is the transmit beam origin location on the array, can be mathematically expressed as given by (15). The receive signal $s_{ch}$ is simply the backscattered signal from the point scatterer at (r,x), attenuated and delayed by the propagation time $T_{rcv}$ from (r,x) back to the transducer receive element at $x'_p$.

$$T_{xmt} = T_{xmt}(x - x_n, r, r_{xmt}) = \frac{r}{c} + \Delta T_{xmt}(x - x_n, r, r_{xmt}) \quad (15)$$

$$T_{rcv} = T_{rcv}(x'_p - x, r) = \frac{\sqrt{r^2 + (x'_p - x)^2}}{c}$$

$$\tilde{s}_{ch}(t - T_{xmt} - T_{rcv}, x'_p, x - x_n, r, r_{xmt}) =$$

$$e^{-j\varphi_d(t)} \int h_{rcv}(t - t', x'_p) \tilde{s}_{xmt}(t' - T_{xmt} - T_{rcv}, x - x_n, r, r_{xmt}) dt'$$

If the transmit excitation by the transducer is represented by $$s_{xmt}(t) = p(t) e^{j\omega_x t} \quad (16)$$

where p(t) is the transmit pulse envelope, potentially complex, and $\omega_x$ is the transmit carrier frequency, then without loss of generality the transmit pulse wavefront can be expressed as $$\tilde{s}_{xmt}(t-T_{xmt},x-x_n,r,r_{xmt}) = \tilde{p}(t-T_{xmt},x-x_n,r,r_{xmt}) e^{j\omega_x(t-T_{xmt})} S_{xmt}(x-x_n,r,r_{xmt},\omega_x) \quad (17)$$

where ~ indicates that the pulse envelope has been modified due to range and position dependent transmit diffraction effects, $\omega_x$ is the effective transmit carrier frequency which may be depth dependent due to frequency dependent attenuation effects, and $S_{xmt}$ represents the transmit beampattern. Upon substitution into equation (15), the receive channel signal becomes $$\tilde{s}_{ch}(t-T_{xmt}-T_{rcv},x'_p,x-x_n,r,r_{xmt}) = \tilde{p}_{rcv}(t-T_{xmt}-T_{rcv},x-x_n,r,r_{xmt}) \cdot e^{-j\phi_d(t)+\omega_c(t-T_{xmt}-T_{rcv})} S_{xmt}(x-x_n,r,r_{xmt},\omega_c) \quad (18)$$

where $\tilde{p}_{rcv}(t-T_{xmt}-T_{rcv},x-x_n,r,r_{xmt})$ includes the effects of transmit diffraction, receive propagation back to the transducer, attenuation, filtering, etc., and $\omega_c$ is the depth dependent receive carrier frequency. Matching the demodulation and receive carrier frequencies results in the baseband channel signal $$\tilde{s}_{ch}(t-T_{xmt}-T_{rcv},x'_p,x-x_n,r,r_{xmt}) = \tilde{p}_{rcv}(t-T_{xmt}-T_{rcv},x-x_n,r,r_{xmt}) \cdot e^{-j\omega_c T_{rcv}} e^{-j\omega_c T_{xmt}} S_{xmt}(x-x_n,r,r_{xmt},\omega_c) \quad (18)$$

Image/Volume Reconstruction I shown in FIG. 7, creates a single channel domain dataset from which the Area Formation block operates on after the Transmit Synthesis block has effectively compressed the transmit beam. Let the transmit synthesis and area formation outputs be given by $$T(x'_p - x_{ij}, r_{ij}) = \frac{r_{ij} + \sqrt{r_{ij}^2 + (x'_p - x_{ij})^2}}{c} \quad (20)$$

$$\tilde{s}_{ch}^{syn}(t - T_{xmt} - T_{rcv}, x'_p, r_{ij}, r, x, r_{xmt}) =$$

$$\underbrace{\sum_{n=\underline{N}_{syn}(r_{ij})} \int h_n^{syn}(t-t', x'_p, r_{ij}) \tilde{s}_{ch}\left(\begin{array}{c} t' - T_{xmt} - T_{rcv}, x'_p, \\ x - x_n, r, r_{xmt} \end{array}\right) dt'}_{\text{Spatial Diffraction Transform}}$$

$$\tilde{s}(r_{ij}, x_{ij}, x) =$$

$$\underbrace{\sum_p a(x'_p - x_{ij}, r_{ij}) \delta\left[\begin{array}{c} t-T \\ x'_p - \\ x_{ij}, r_{ij} \end{array}\right] e^{j\phi(r_{ij}, x'_p - x_{ij})} \tilde{s}_{ch}^{syn}\left(\begin{array}{c} t - T_{xmt} - \\ T_{rcv}, x'_p, r_{ij} \\ r, x, r_{xmt} \end{array}\right)}_{\text{Area Formation}}$$

Inserting equation (19) into equation (20) yields an expression for the synthesized channel signals, namely $$\tilde{s}_{ch}^{syn}(t - T_{xmt} - T_{rcv}, x'_p, r_{ij}, r, x, r_{xmt}) = \qquad (21)$$

$$\sum_{n=\underline{N}_{syn}(r_{ij})} \int h_n^{syn}(t - t', x'_p, r_{ij}) \tilde{p}_{rcv}(t' - T_{xmt} - T_{rcv}, x - x_n, r, r_{xmt})$$

$$e^{-j\omega_c T_{rcv}} e^{-j\omega_c T_{xmt}} S_{xmt}(x - x_n, r, r_{xmt}, \omega_c) dt'$$

Consider three different functional forms for the transmit synthesis filters $h_n^{syn}$, namely $$h_n^{syn}(t, x'_p, r_{ij}) = \begin{cases} h^{syn}(x_n - x_{ij}, r_{ij}, r_{xmt})\delta(t) \\ h^{syn}(x_n - x_{ij}, r_{ij}, r_{xmt})\delta \\ \quad [t + \Delta T_{xmt}(x_n - x_{ij}, r_{ij}, r_{xmt})] \\ h^{syn}\begin{bmatrix} t + \Delta T_{xmt}(x_n - x_{ij}, r_{ij}, r_{xmt}), \\ x_n - x_{ij}, r_{ij}, r_{xmt} \end{bmatrix} \end{cases} \qquad (22)$$

These transmit synthesis filter forms: a) are lateral convolution filters, and b) depend upon image range coordinate $r_{ij}$ relative to transmit focus range $r_{xmt}$ so as to provide range dependent transmit beam diffraction correction. The $N_{syn}$ filters of $h^{syn}$ are approximately centered around the $n^{th}$ transmit beam closest to the lateral image coordinate $x_{ij}$, and are designed in such a manner as to correct for the amplitude variations and range r dependent approximate quadratic delay/phase error experienced by the received backscattered signals as the transmit beam is translated across the region of interest, i.e., a spatial chirp compression filter. The number of filters necessary to provide complete spatial compression varies with depth r and hence, image coordinate $r_{ij}$, being dependent upon how wide the defocused transmit beam is, which is based upon how far r is from the transmit focus range $r_{xmt}$. The wider the defocused transmit beam, the greater the number of filters required for full spatial compression. To the extent that a limited number of filters are used due to fixed computational resources or otherwise, the transmit beam only be partially compressed, which in many cases can suppress receive sidelobe clutter dramatically. For image coordinate locations $r_{ij}$ around the transmit focus range $r_{xmt}$, not many filters are required since the transmit beam is nearly focused.

The lateral convolution form of these transmit synthesis filters provides an effective lateral spatial shifting of the transmit beam, from the combination of spatial transmit beam firings, to center the synthesized transmit beam over the image coordinate location $x_{ij}$. This property effectively decouples transmit and round-trip spatial sampling requirements, while creating a transmit beam centered over the desired image location. This property is achievable provided that the transmit beams satisfy spatial Nyquist sampling requirements. Optimal design of the transmit synthesis filters requires sufficiently predictable temporal and spatial pre-detection, i.e., coherent, characteristics of both the actual transmit beams and the desired synthesized transmit beams as they are swept through the region of interest, whether electronically or mechanically scanned, or any combination thereof, as well as taking into account the number of synthesis filters $N_{syn}$ used at a given image coordinate location. In general, the filtering of signals can yield different results depending upon whether the signal of interest is coherent, i.e., backscattered signals from the region of interest, or incoherent in origin, i.e., random noise, and produce changes in the signal to noise ratio (SNR). Since these transmit synthesis filters will process channel domain data from multiple transmit beams, each of which will contain receive front-end random noise, optimal design of the transmit synthesis filters may also include these effects.

The first form of $h_n^{syn} = h^{syn}(x_n - x_{ij}, r_{ij}, r_{xmt})\delta(t)$ represents a range dependent, complex lateral filter, i.e., magnitude/phase, real/imaginary, etc., which is independent of time and simply provides an amplitude weighted phase adjustment of the transmit beam dependent channel domain data sets prior to transmit synthesis summation. Referring to FIG. 7 which shows a representation of the receive channel signals across transmit firings for a point scatterer which lies shallow to the transmit focus range, i.e., $r = r_a < r_{xmt}$, the backscattered receive signals arrive earlier as the transmit beam is laterally translated away from the position of the point scatterer at (r,x) due to the converging transmit pulse wavefront. The weighted phase adjustment is sufficient provided that the delay excursion of the transmit pulse wavefront, for the spatial portion of the defocused transmit beam to be compressed, or refocused, is on the order of the round-trip pulse length or less.

The second form of $h_n^{syn} = h^{syn}(x_n - x_{ij}, r_{ij}, r_{xmt})\delta[t + \Delta T_{xmt}(x_n - x_{ij}, r_{ij}, r_{xmt})]$ represents a range dependent, complex lateral filter as well; however, in addition to an amplitude weighted phase adjustment of the transmit beam dependent channel domain data sets prior to transmit synthesis summation, it provides a differential time delay correction $\Delta T_{xmt}(x_n - x_{ij}, r_{ij}, r_{xmt})$ (refer to equation (15)) to the backscattered receive channel signals as the transmit beam is laterally translated away from the position of the point scatterer at (r,x) due to the converging/diverging transmit pulse wavefront. This additional time correction will be required when the delay excursion of the transmit pulse wavefront, for the spatial portion of the defocused transmit beam to be compressed, or refocused, begins to exceed the round-trip pulse length.

The third form of $h_n^{syn} = h^{syn}[t + \Delta T_{xmt}(x_n - x_{ij}, r_{ij}, r_{xmt}), x_n - x_{ij}, r_{ij}, r_{xmt}]$ represents a range dependent, complex lateral filter as well; however, in addition to an amplitude weighted phase adjustment and differential time delay correction $\Delta T_{xmt}(x_n - x_{ij}, r_{ij}, r_{xmt})$ applied to the receive channel signals, the temporal filter portion also provides a range and lateral position dependent pulse shape correction. The intent is to compensate the receive channel signals $\tilde{s}_{ch}(t - T_{xmt} - T_{rcv}, x'_p, x - x_n, r, r_{xmt})$, and through extension, the transmit signal $\tilde{s}_{xmt}(t - T_{xmt}, x - x_n, r, r_{xmt})$, for diffraction effects away from the transmit focus, receive filtering, etc., in addition to differential transmit delay correction and transmit refocusing.

Substitution of the first form of $h_n^{syn} = h^{syn}(x_n - x_{ij}, r_{ij}, r_{xmt})\delta(t)$ into the synthesized channel data given by equation (21), along with equation (15) yields $$\tilde{s}_{ch}^{syn}(t - T_{xmt} - T_{rcv}, x'_p, x_{ij}, r_{ij}, x, r, r_{xmt}) = e^{-j\omega_c(\frac{r}{c} + T_{rcv})} \qquad (23)$$

$$\sum_{n=\underline{N}_{syn}(r_{ij})} h^{syn}(x_n - x_{ij}, r_{ij}, r_{xmt}) \tilde{p}_{rcv}(t - T_{xmt} - T_{rcv}, x - x_n, r, r_{xmt})$$

$$e^{-j\omega_c \Delta T_{xmt}} S_{xmt}(x - x_n, r, r_{xmt}, \omega_c)$$

In order to determine a solution for the transmit synthesis filter coefficients, they may be derived based upon theoretical considerations, i.e., deriving a spatial compression filter analogous to linear FM chirp pulse compression, or an error function of the following form can be minimized at each image location $(r_{ij}, x_{ij})$, over point scatterer lateral locations x, using the list of potential range/position dependent $\underline{N}_{syn}(r_{ij},x_{ij})$ transmit beams, generally centered about the transmit beam closest to $x_{ij}$, i.e., $x_0(x_{ij})$:

$$\varepsilon^2 = \qquad (24)$$

$$\sum_x \left| \sum_{n=\underline{N}_{syn}(r_{ij})} \{ h^{syn}(x_n - x_{ij}, r_{ij}, r_{xmt}) \tilde{p}_{rcv}[-\Delta T_{xmt}(x-x_n, r_{ij}, r_{xmt}), \right.$$

$$x - x_n, r, r_{xmt}] \cdot e^{-j\omega_c \Delta T_{xmt}(x-x_n, r_{ij}, r_{xmt})}$$

$$S_{xmt}(x - x_n, r_{ij}, r_{xmt}, \omega_c) \} -$$

$$\left. p^{desired}(0, x - x_{ij}, r_{ij}) S_{xmt}^{desired}(x - x_{ij}, r_{ij}, r_{xmt}, \omega_c) \right|^2$$

where $$p^{desired}\left(t - \frac{2r_{ij}}{c}, x - x_{ij}, r_{ij}\right)$$

and $s_{xmt}^{desired}(\ldots)$ are defined as the desired transmit pulse response and desired beampattern respectively, or taken together—the desired transmit point spread function, which is the targeted response for the spatial diffraction transform. t is evaluated at the nominal receive time $t=2r/c$ (see FIG. 6), r is evaluated at the image range coordinate $r_{ij}$, receive channel location $x'_p$ is evaluated at the point scatterer location x. If $S_{xmt}^{desired}(\ldots)$ is that of a continuous focused transmit beam, then the subsequent transmit synthesis filter coefficients derived through error minimization or other means, will provide spatial compression of the transmit beam away from the focus, in addition to the spatial shifting property. Multiple time locations t can also be used in evaluating $\tilde{p}_{rcv}(\ldots)$, $S_{xmt}(\ldots)$, and $e^{-j\omega_c \Delta T_{xmt}}$ in equation (23) in forming the error function, as well as $p^{desired}(\ldots)$. Other error functions are possible. For one skilled in the art, there are many ways in which to perform this error minimization, for example a least-squares, weighted least-squares, constrained least-squares error minimization, etc., where a set of simultaneous linear equations are created from the error function, and the unknown coefficients $h_n^{syn} = h^{syn}(n)$ are solved. For a fixed number of transmit synthesis filters $N_{syn}(r_{ij}, x_{ij})$, error minimization provides for a flexible solution. Evaluation of the receive pulse waveform(s) $\tilde{p}_{rcv}(\ldots)$, transmit beampattern $S_{xmt}(\ldots)$, desired pulse response $p^{desired}(\ldots)$ and beampattern $S_{xmt}^{desired}(\ldots)$, and transmit differential time delay $\Delta T_{xmt}(\ldots)$ in the error minimization can be performed either through experimental measurement, simulation, or a combination thereof, provided they are sufficiently predictable. Applying the optimized transmit synthesis filter coefficients to the receive channel signals produces synthesized channel data given by $$\tilde{s}_{ch}^{syn}(t - T_{xmt} - T_{rcv}, x'_p, x_{ij}, r_{ij}, x, r, r_{xmt}) \approx \qquad (25)$$

$$e^{-j\omega_c \left(\frac{r}{c} + T_{rcv}\right)} \tilde{p}_{rcv}\left\{t - \Delta T_{xmt}[x_{ij} - x_0(x_{ij})] - \left(\frac{r}{c} + T_{rcv}\right), \right.$$

$$\left. x - x_0(x_{ij}), r, r_{xmt} \right\} S_{xmt}^{syn}(x - x_{ij}, r_{ij}, r, r_{xmt}, \omega_c)$$

where the synthesized transmit beampattern is given by $$S_{xmt}^{syn}(x - x_{ij}, r_{ij}, r, r_{xmt}, \omega_c) = \sum_{n=\underline{N}_{syn}(r_{ij})} h^{syn}(x_n - x_{ij}, r_{ij}, r_{xmt}) \qquad (26)$$

$$e^{-j\omega_c \Delta T_{xmt}(x-x_n, r, r_{xmt})} S_{xmt}(x - x_n, r, r_{xmt}, \omega_c)$$

Note that the synthesized transmit beampattern will be centered over the image coordinate location $x_{ij}$ as described previously.

Upon substituting equation (25) into the expression for the Area Formation block output given by equation (20), an expression is obtained for the round-trip point spread function $$\tilde{s}(r_{ij}, r, x_{ij}, x) \approx \sum_p a(x'_p - x_{ij}, r_{ij}) e^{j\phi(r_{ij}, x'_p - x_{ij})} e^{-j\omega_c\left(\frac{r}{c} + T_{rcv}\right)} \cdot \tilde{p}_{rcv} \qquad (27)$$

$$\left\{\frac{2(r_{ij} - r)}{c} - \Delta T_{xmt}[x_{ij} - x_0(x_{ij})], x - x_0(x_{ij}), r, r_{xmt}\right\}$$

$$S_{xmt}^{syn}(x - x_{ij}, r_{ij}, r, r_{xmt}, \omega_c)$$

where the area formation element dependent delay $T(x'_p - x_{ij}, r_{ij})$ has effectively cancelled the element dependent receive delay $T_{rcv}(x'_p - x, r)$ given in equation (15), for $r_{ij} \sim r$. Then, $$\tilde{s}(r_{ij} - r, x_{ij} - x, r_{ij}, x_{ij}) \approx \qquad (28)$$

$$e^{-j\omega_c \frac{2r}{c}} \tilde{p}_{rcv}\left\{\frac{2(r_{ij} - r)}{c} - \Delta T_{xmt}[x_{ij} - x_0(x_{ij})], x - x_0(x_{ij}), r, r_{xmt}\right\} \cdot$$

$$S_{xmt}^{syn}(x - x_{ij}, r_{ij}, r, r_{xmt}, \omega_c) S_{rcv}(x - x_{ij}, r_{ij}, r, \omega_c)$$

where the round-trip point spread function's parameters are meant to indicate that it is in the form of a convolution kernel which could vary slowly throughout the imaging region defined by $(r_{ij}, x_{ij})$. The receive beampattern $S_{rcv}(\ldots)$ is given by $$S_{rcv}(x - x_{ij}, r_{ij}, r, \omega_c) = \sum_p a(x'_p - x_{ij}, r_{ij}) e^{j\phi(r_{ij}, x'_p - x_{ij})} e^{-j\omega_c\left(T_{rcv} - \frac{r}{c}\right)} \qquad (29)$$

In order to correct for receive element phase errors due to the differing propagation paths from the point scatterer back to the transducer array, the receive phase is given by $$\phi(r_{ij}, x'_p - x_{ij}) = \qquad (30)$$

$$\omega_c\left[T(x'_p - x_{ij}, r_{ij}) - \frac{2r_{ij}}{c}\right] = \omega_c\left[\frac{\sqrt{r_{ij}^2 + (x'_p - x_{ij})^2} - r_{ij}}{c}\right]$$

Substituting equation (30) into equation (29) yields an expression for the receive beampattern $$S_{rcv}(x - x_{ij}, r_{ij}, r, \omega_c) = \qquad (31)$$

$$\sum_p a(x'_p - x_{ij}, r_{ij}) e^{j\omega_c \left[\frac{\sqrt{r_{ij}^2 + (x'_p - x_{ij})^2} - r_{ij}}{c} - \frac{\sqrt{r^2 + (x'_p - x)^2} - r}{c}\right]}$$

-continued $$S_{rcv}(x - x_{ij}, r_{ij}, \omega_c) \approx$$

$$e^{-j\omega_c \frac{1}{2c} \frac{(x-x_{ij})^2}{r}} \sum_p a(u_p, r_{ij}) e^{-j\omega_c \frac{u^2}{2c}\left(\frac{1}{r} - \frac{1}{r_{ij}}\right)} e^{j\omega_c \frac{(x-x_{ij})u}{r_{ij}c}}$$

where a Taylor series expansion of the phase was used in the approximation and yields the well known Fourier transform of the receive apodization for $r_{ij}$=r, i.e., in the focal plane. Note the expression for the round-trip point spread function given by equation (28) is in the form of a linear convolution kernel in both image coordinates, with a slow variation in characteristics due to the remaining parameter dependencies. The parameter dependencies uncorrected by the first form of the transmit synthesis filters equation (22) are: a) the uncorrected spatially dependent differential transmit delay, and b) the transmit diffraction and receive filtering effects on the transmit pulse. These are addressed with the second and third forms of the transmit synthesis filters given by equation (22) respectively.

Substituting the second form of $h_n^{syn} = h^{syn}(x_n - x_{ij}, r_{ij}, r_{xmt}) \delta[t + \Delta T_{xmt}(x_n - x_{ij}, r_{ij}, r_{xmt})]$ into the synthesized channel data given by equation (21), along with equation (15) yields $$\tilde{s}_{ch}^{syn}(t - T_{rcv}, x'_p, x_{ij}, r_{ij}, x, r, r_{xmt}) \approx \quad (32)$$

$$e^{-j\omega_c\left(\frac{r}{c} + T_{rcv}\right)} \sum_{n=N_{syn}(r_{ij})} h^{syn}(x_n - x_{ij}, r_{ij}, r_{xmt})$$

$$\tilde{p}_{rcv}(t - T_{rcv}, x - x_n, r, r_{xmt}) e^{-j\omega_c \Delta T_{xmt}} S_{xmt}(x - x_n, r, r_{xmt}, \omega_c)$$

where the differential transmit delay is effectively cancelled for $x_{ij} \sim x$. Solving for the transmit synthesis filter coefficients, the following error equation is minimized for each image location ($r_{ij}, x_{ij}$), over point scatterer lateral locations x as before.

$$\varepsilon^2 = \sum_x \left| \sum_{n=N_{syn}(r_{ij})} \{h^{syn}(x_n - x_{ij}, r_{xmt}) \tilde{p}_{rcv}(0, x - x_n, r_{ij}, r_{xmt}) \right. \quad (33)$$

$$e^{-j\omega_c \Delta T_{xmt}(x-x_n, r_{ij}, r_{xmt})} S_{xmt}(x - x_n, r_{ij}, r_{xmt}, \omega_c)\} -$$

$$\left. p^{desired}(0, x - x_{ij}, r_{ij}) S_{xmt}^{desired}(x - x_{ij}, r_{ij}, r_{xmt}, \omega_c) \right|^2$$

where time t is evaluated at the nominal receive time t=2r/c (see FIG. 6). Note that since the differential transmit delay $\Delta T_{xmt}(\ldots)$ has been corrected, the pulse signals on a given receive channel are aligned in time, i.e., sampling along the transmit delay arc.

As before, multiple time locations can be used in constructing the error function. Applying the optimized transmit synthesis filter coefficients to the receive channel signals produces synthesized channel data given by $$\tilde{s}_{ch}^{syn}(t - T_{rcv}, x'_p, x_{ij}, r_{ij}, x, r, r_{xmt}) \approx \quad (34)$$

$$e^{-j\omega_c\left(\frac{r}{c} + T_{rcv}\right)} \tilde{p}_{rcv}[t, x - x_0(x_{ij}), r, r_{xmt}] S_{xmt}^{syn}(x - x_{ij}, r_{ij}, r, r_{xmt}, \omega_c)$$

where the synthesized transmit beampattern is given by $$S_{xmt}^{syn}(x - x_{ij}, r_{ij}, r, r_{xmt}, \omega_c) = \sum_{n=N_{syn}(r_{ij})} h^{syn}(x_n - x_{ij}, r_{ij}, r_{xmt}) \quad (35)$$

$$e^{-j\omega_c \Delta T_{xmt}(x-x_n, r, r_{xmt})} S_{xmt}(x - x_n, r, r_{xmt}, \omega_c)$$

Note that even though the differential transmit delay has been corrected, a phase error due to the transmit delay still exists due to demodulation being performed prior to the correction. Note further that the synthesized transmit beampattern is now centered over the image coordinate location as before.

Upon substituting equation (34) into the expression for the Area Formation block output given by equation (20), an expression is obtained for the round-trip point spread function $$\tilde{s}(r_{ij}, r, x_{ij}, x) \approx \sum_p a(x'_p - x_{ij}, r_{ij}) e^{j\phi(r_{ij}, x'_p - x_{ij})} \quad (36)$$

$$e^{-j\omega_c\left(\frac{r}{c} + T_{rcv}\right)} \cdot \tilde{p}_{rcv}\left[\frac{2(r_{ij} - r)}{c}, x - x_0(x_{ij}), r, r_{xmt}\right]$$

$$S_{xmt}^{syn}(x - x_{ij}, r_{ij}, r, r_{xmt}, \omega_c)$$

where the Area Formation element dependent delay $T(x'_p - x_{ij}, r_{ij})$ has effectively cancelled the element dependent receive delay $T_{rcv}(x'_p - x, r)$ given in equation (15), for $r_{ij} \sim r$. Then, $$\tilde{s}(r_{ij} - r, x_{ij} - x, r_{ij}, x_{ij}) \approx e^{-j\omega_c \frac{2r}{c}} \quad (37)$$

$$\tilde{p}_{rcv}\left[\frac{2(r_{ij} - r)}{c}, x - x_0(x_{ij}), r, r_{xmt}\right] \cdot S_{xmt}^{syn}(x - x_{ij}, r_{ij}, r, r_{xmt}, \omega_c)$$

$$S_{rcv}(x - x_{ij}, r_{ij}, r, \omega_c)$$

where the receive beampattern $s_{rcv}(\ldots)$ is the same as before, given by equations (29)-(31).

Substituting the third form of $h_n^{syn} = h^{syn}[t + \Delta T_{xmt}(x_n - x_{ij}, r_{ij}, r_{xmt}), x_n - x_{ij}, r_{ij}, r_{xmt}]$ into the synthesized channel data given by equation (21), using variable substitution along with equation (15) yields $$\tilde{s}_{ch}^{syn}(t - T_{rcv}, x'_p, x_{ij}, r_{ij}, x, r, r_{xmt}) \approx \quad (38)$$

$$e^{-j\omega_c\left(\frac{r}{c} + T_{rcv}\right)} \cdot \sum_{n=N_{syn}(r_{ij})} \int h^{syn}[t - t', x_n - x_{ij}, r_{ij}, r_{xmt}] \tilde{p}_{rcv}(t' - T_{rcv},$$

$$x - x_n, r, r_{xmt}) e^{-j\omega_c \Delta T_{xmt}} S_{xmt}(x - x_n, r, r_{xmt}, \omega_c) dt'$$

Solving for the transmit synthesis filter coefficients assuming a finite number of discrete time samples $t_m$, m=[0, 1, ... M-1], the following error equation needs to be minimized, for each image location ($r_{ij}, x_{ij}$), over point scatterer lateral locations x and time t $$\varepsilon' = \sum_t \sum_x \left| \quad (39) \right.$$

-continued $$\sum_{n=\underline{N}_{syn}(r_{ij})} \left\{ \sum_{m'=0}^{M-1} \{h^{syn}(t-t_{m'}, x_n - x_{ij}, r_{ij}, r_{xmt}) \tilde{p}_{rcv}(t_{m'}, x - x_n, r_{ij}, r_{xmt})\} \right.$$

$$\left. e^{j\omega_c \Delta T_{xmt}(x-x_n, r_{ij}, r_{xmt})} S_{xmt}(x - x_n, r_{ij}, r_{xmt}, \omega_c) \right\} -$$

$$\left. p^{desired}(t, x - x_{ij}, r_{ij}) S_{xmt}^{desired}(x - x_{ij}, r_{ij}, r_{xmt}, \omega_c) \right|^2$$

where time t' is evaluated around the nominal receive time t'=2r/c (see FIG. 6). Note that since the differential transmit delay $\Delta T_{xmt}(\ldots)$ has been corrected, the pulse signals on a given receive channel are aligned in time, i.e., sampling along the transmit delay arc. In addition, the time dependence of the desired transmit pulse response $p^{desired}(t,x-x_{ij},r_{ij})$ appears in the error minimization function. A set of simultaneous linear equations are created from the error function, and the unknown coefficients $h_{mn}^{syn}=h^{syn}(m,n)$ are solved. Thus, the transmit synthesis coefficients will attempt to correct the round-trip temporal response for transmit diffraction effects as well as receive filtering. Applying the optimized transmit synthesis filter coefficients to the receive channel signals produces synthesized channel data given by $$s_{ch}^{syn}(t - T_{rcv}, x'_p, x_{ij}, r_{ij}, x, r, r_{xmt}) \approx \quad (40)$$

$$e^{-j\omega_c(\frac{r}{c}+T_{rcv})} p^{syn}(t, x - x_{ij}, r_{ij}) S_{xmt}^{syn}(x - x_{ij}, r_{ij}, r, r_{xmt}, \omega_c)$$

where the synthesized transmit point spread function is given by $$p^{syn}(t, x - x_{ij}, r_{ij}) S_{xmt}^{syn}(x - x_{ij}, r_{ij}, r, r_{xmt}, \omega_c) \approx \quad (41)$$

$$\sum_{n=\underline{N}_{syn}(r_{ij})} \sum_{m'=0}^{M-1} \{h^{syn}(t-t_{m'}, x_n - x_{ij}, r_{ij}, r_{xmt}) \tilde{p}_{rcv}(t_{m'}, x - x_n, r, r_{xmt})\}$$

$$e^{-j\omega_c \Delta T_{xmt}(x-x_n, r, r_{xmt})} S_{xmt}(x - x_n, r, r_{xmt}, \omega_c)$$

Upon substituting equation (40) into the expression for the Area Formation block output given by equation (20), an expression is obtained for the round-trip point spread function $$s(r_{ij}, r, x_{ij}, x) \approx \sum_p a(x'_p - x_{ij}, r_{ij}) e^{j\phi(r_{ij}, x'_p - x_{ij})} e^{j\omega_c(\frac{r}{c}+T_{rcv})} \quad (42)$$

$$p^{syn}\left[\frac{2(r_{ij}-r)}{c}, x - x_{ij}, r_{ij}\right] S_{xmt}^{syn}(x - x_{ij}, r_{ij}, r, r_{xmt}, \omega_c)$$

where the Area Formation element dependent delay $T(x'_p-x_{ij},r_{ij})$ has effectively cancelled the element dependent receive delay $T_{rcv}(x'_p-x,r)$ given in equation (15), for r. Then, $$s(r_{ij} - r, x_{ij} - x, r_{ij}, x_{ij}) \approx e^{-j\omega_c \frac{2r}{c}} p^{syn}\left[\frac{2(r_{ij}-r)}{c}, x - x_{ij}, r_{ij}\right] \quad (43)$$

$$S_{xmt}^{syn}(x - x_{ij}, r_{ij}, r, r_{xmt}, \omega_c) S_{rcv}(x - x_{ij}, r_{ij}, r, \omega_c)$$

where the receive beampattern $s_{rcv}(\ldots)$ is the same as before, given by equations (29)-(31). Thus, using the more general transmit synthesis filter form, both differential time delay correction and pulse shape correction can be obtained simultaneously.

Image/Volume Reconstruction II shown in FIG. 8, which is a rearrangement of the Area Formation and Transmit Synthesis blocks, the Area Formation block operates separately on channel domain datasets, from which the Transmit Synthesis block effectively compresses the transmit beam across multiple area formed outputs. Let the area formation and transmit synthesis outputs be given by $$T(x'_p - x_{ij}, r_{ij}) = \frac{r_{ij} + \sqrt{r_{ij}^2 + (x'_p - x_{ij})^2}}{c} \quad (44)$$

$$\tilde{s}_n(r_{ij}, r, x_{ij}, x) = \underbrace{\sum_p a(x'_p - x_{ij}, r_{ij}) \delta[t - T(x'_p - x_{ij}, r_{ij})] e^{j\phi(r_{ij}, x'_p - x_{ij})}}_{\text{Area Formation}}$$

$$\tilde{s}_{ch}(t - T_{xmt} - T_{rcv}, x'_p, x - x_n, r, r_{xmt})$$

$$\tilde{s}(r_{ij}, r, x_{ij}, x) = \underbrace{\sum_{n=\underline{N}_{syn}(r_{ij})} \sum_{r'_{ij}} h_n^{syn}(x_n - x_{ij}, r_{ij} - r'_{ij}, r_{ij}) \tilde{s}_n(r'_{ij}, r, x_{ij}, x)}_{\text{Spatial Diffraction Transform}}$$

Inserting equation (19) into equation (44) yields an expression for the area formation outputs, namely $$\tilde{s}_n(r_{ij}, r, x_{ij}, x) = \sum_p a(x'_p - x_{ij}, r_{ij}) \delta[t - T(x'_p - x_{ij}, r_{ij})] \quad (45)$$

$$e^{j\phi(r_{ij}, x'_p - x_{ij})} \tilde{p}_{rcv}(t - T_{xmt} - T_{rcv}, x - x_n, r, r_{xmt})$$

$$e^{-j\omega_c T_{rcv}} e^{-j\omega_c T_{xmt}} S_{xmt}(x - x_n, r, r_{xmt}, \omega_c)$$

Simplifying equation (45), along with equation (15) yields $$\tilde{s}_n(r_{ij}, r, x_{ij}, x) \approx \sum_p a(x'_p - x_{ij}, r_{ij}) e^{j\phi(r_{ij}, x'_p - x_{ij})} e^{-j\omega_c(\frac{r}{c}+T_{rcv})} \quad (46)$$

$$\tilde{p}_{rcv}\left[\frac{2(r_{ij}-r)}{c} - \Delta T_{xmt}(x - x_n, r, r_{xmt}), x - x_n, r, r_{xmt}\right]$$

$$e^{-j\omega_c \Delta T_{xmt}} S_{xmt}(x - x_n, r, r_{xmt}, \omega_c)$$

where the area formation element dependent receive delay $T(x'_p-x_{ij},r_{ij})$ has effectively cancelled the element dependent receive delay $T_{rcv}(x'_p-x,r)$ given in equation (15), for $r_{ij}\sim r$. Then, $$\tilde{s}_n(r_{ij}, r, x_{ij}, x) \approx \quad (47)$$

$$e^{-j\omega_c \frac{2r}{c}} \tilde{p}_{rcv}\left[\frac{2(r_{ij}-r)}{c} - \Delta T_{xmt}(x - x_n, r, r_{xmt}), x - x_n, r, r_{xmt}\right]$$

$$S_{rcv}(x - x_{ij}, r_{ij}, r, \omega_c) e^{-j\omega_c \Delta T_{xmt}} S_{xmt}(x - x_n, r, r_{xmt}, \omega_c)$$

where the receive beampattern $S_{rcv}(\ldots)$ is given by $$S_{rcv}(x-x_{ij},r_{ij},r,\omega_c) = \sum_p a(x'_p-x_{ij},r_{ij})e^{j\phi(r_{ij},x'_p-x_{ij})}e^{-j\omega_c\left(T_{rcv}-\frac{r}{c}\right)} \quad (48)$$

which is identical to equation (29). In order to correct for receive element phase errors due to the differing propagation paths from the point scatterer back to the transducer array, the receive phase is given by equation (30) (repeated here for convenience)

$$\phi(r_{ij},x'_p-x_{ij}) = \omega_c\left[T(x'_p-x_{ij},r_{ij})-\frac{2r_{ij}}{c}\right] \quad (49)$$

$$= \omega_c\left[\frac{\sqrt{r_{ij}^2+(x'_p-x_{ij})^2}-r_{ij}}{c}\right]$$

Substituting equation (49) into equation (48) yields an expression for the receive beampattern $$S_{rcv}(x-x_{ij},r_{ij},r,\omega_c) = \quad (50)$$

$$\sum_p a(x'_p-x_{ij},r_{ij})e^{j\omega_c\left[\frac{\sqrt{r_{ij}^2+(x'_p-x_{ij})^2}-r_{ij}}{c}-\frac{\sqrt{r^2+(x'_p-x)^2}-r}{c}\right]}$$

$$S_{rcv}(x-x_{ij},r_{ij},r,\omega_c) \approx$$

$$e^{j\omega_c\frac{1}{2c}\frac{(x-x_{ij})^2}{r}}\sum_p a(u_p,r_{ij})e^{-j\omega_c\frac{u^2}{2c}\left(\frac{1}{r}-\frac{1}{r_{ij}}\right)}e^{j\omega_c\frac{(x-x_{ij})u}{r_{ij}c}}$$

where a Taylor series expansion of the phase was used in the approximation and yields the well known Fourier transform of the receive apodization for $r_{ij}=r$, i.e., in the focal plane.

Proceeding in an analogous manner as for Image/Volume Reconstruction I, consider three different functional forms for the transmit synthesis filters $h_n^{syn}$, namely $$h_n^{syn}(r_{ij}) = \begin{cases} h^{syn}(x_n-x_{ij},r_{ij},r_{xmt})\delta(r_{ij}) & (51) \\ h^{syn}(x_n-x_{ij},r_{ij},r_{xmt})\delta\left[r_{ij}+\frac{c}{2}\Delta T_{xmt}(x_n-x_{ij},r_{ij},r_{xmt})\right] \\ h^{syn}\left[x_n-x_{ij},r_{ij}+\frac{c}{2}\Delta T_{xmt}(x_n-x_{ij},r_{ij},r_{xmt}),r_{xmt}\right] \end{cases}$$

These transmit synthesis filter forms: a) are lateral convolution filters, and b) depend upon image range coordinate $r_{ij}$ relative to transmit focus range $r_{xmt}$ so as to provide range dependent transmit beam diffraction correction. However, these filters, in contrast to those given by equation (22), operate on area/volume formed data as opposed to channel data. As before, the $N_{syn}$ filters of $h^{syn}$ are approximately centered around the $n^{th}$ transmit beam closest to the lateral image coordinate $x_{ij}$, and are designed in such a manner as to correct for the amplitude variations and range r dependent approximate quadratic delay/phase error experienced by the received backscattered signals as the transmit beam is translated across the region of interest, i.e., a spatial chirp compression filter. The number of filters necessary to provide complete spatial compression varies with depth r and hence, image coordinate $r_{ij}$, being dependent upon how wide the defocused transmit beam is, which is based upon how far r is from the transmit focus range $r_{xmt}$. However, note that with the Transmit Synthesis block following the Area Formation block, the transmit synthesis filters do not have the opportunity to correct for variations on a receive channel basis since the filters operate on channel summed outputs.

The lateral convolution form of these transmit synthesis filters provides an effective lateral spatial shifting of the transmit beam, from the combination of spatial transmit beam firings, to center the synthesized transmit beam over the image coordinate location $x_{ij}$. This property effectively decouples transmit and round-trip spatial sampling requirements, while creating a transmit beam centered over the desired image location. This property is achievable provided that the transmit beams satisfy spatial Nyquist sampling requirements. Optimal design of the transmit synthesis filters requires sufficiently predictable temporal and spatial pre-detection, i.e., coherent, characteristics of both the actual transmit beams and the desired synthesized transmit beams as they are swept through the region of interest, whether electronically or mechanically scanned, or any combination thereof, as well as taking into account the number of synthesis filters $N_{syn}$ used at a given image coordinate location. In general, the filtering of signals can yield different results depending upon whether the signal of interest is coherent, i.e., backscattered signals from the region of interest, or incoherent in origin, i.e., random noise, and produce changes in the signal to noise ratio (SNR). Since these transmit synthesis filters will process area formed data from multiple transmit beams, each of which will contain receive front-end random noise, optimal design of the transmit synthesis filters may also include these effects.

The first form of $h_n^{syn}=h^{syn}(x_n-x_{ij},r_{ij},r_{xmt})\delta(r_{ij})$, represents a range dependent, complex lateral filter, i.e., magnitude/phase, real/imaginary, etc., simply provides an amplitude weighted phase adjustment of the area formed data prior to transmit synthesis summation. Referring to FIG. 7 which shows a representation of the receive channel signals across transmit firings for a point scatterer which lies shallow to the transmit focus range, i.e., $r=r_a<r_{xmt}$, the backscattered receive signals arrive earlier as the transmit beam is laterally translated away from the position of the point scatterer at (r,x) due to the converging transmit pulse wavefront. The weighted phase adjustment is sufficient provided that the delay excursion of the transmit pulse wavefront, for the spatial portion of the defocused transmit beam to be compressed, or refocused, is on the order of the round-trip pulse length or less. Due to the differential transmit delay excursion, receive focusing errors may result due to the time dependent nature of the dynamic receive area formation or beamformation process. However, receive focusing errors will not be large if $$\frac{c}{2}\Delta T_{xmt}(x-x_n,r,r_{xmt})$$

is within the receive focusing depth of field limits. Since the differential transmit delay will not be corrected with this filter form, the area formed outputs will be delayed by the differential transmit delay—a range displacement error of $$\frac{c}{2}\Delta T_{xmt}(x-x_n,r,r_{xmt}).$$

The second form of $$h_n^{syn} = h^{syn}(x_n - x_{ij}, r_{ij}, r_{xmt})\delta\left[r_{ij} + \frac{c}{2}\Delta T_{xmt}(x_n - x_{ij}, r_{ij}, r_{xmt})\right],$$

represents a range dependent, complex lateral filter as well; however, in addition to an amplitude weighted phase adjustment of the transmit beam dependent area formed data prior to transmit synthesis summation, it includes a range displacement correction $$\frac{c}{2}\Delta T_{xmt}(x_n - x_{ij}, r_{ij}, r_{xmt})$$

(refer to equation (15)) to the backscattered receive channel signals as the transmit beam is laterally translated away from the position of the point scatterer at (r,x) due to the converging/diverging transmit pulse wavefront. This additional range displacement correction will be required when the delay excursion of the transmit pulse wavefront, for the spatial portion of the defocused transmit beam to be compressed, or refocused, begins to exceed the round-trip pulse length. Note that while the range displacement errors are corrected, any receive focusing errors are not.

The third form of $$h_n^{syn} = h^{syn}\left[x_n - x_{ij}, r_{ij} + \frac{c}{2}\Delta T_{xmt}(x_n - x_{ij}, r_{ij}, r_{xmt}), r_{xmt}\right],$$

represents a range dependent, complex lateral filter as well; however, in addition to an amplitude weighted phase adjustment, it includes a range displacement correction of $$\frac{c}{2}\Delta T_{xmt}(x_n - x_{ij}, r_{ij}, r_{xmt}).$$

the transmit synthesis filter also provides a range and lateral position dependent pulse shape correction, however, operating on the area formed output range samples. The intent is to compensate the area formed outputs and through extension, the receive channel signals $\tilde{s}_{ch}(t-T_{xmt}-T_{rcv},x'_p,x-x_n,r,r_{xmt})$, as well as the transmit signal $\tilde{s}_{xmt}(t-T_{xmt},x-x_n,r,r_{xmt})$, for diffraction effects away from the transmit focus, receive filtering, etc., in addition to range displacement correction and transmit refocusing. Note that while the range displacement errors are corrected, any receive focusing errors are not.

Substitution of the first form of $h_n^{syn}=h^{syn}(x_n-x_{ij},r_{ij},r_{xmt})\delta(r_{ij})$ into the transmit synthesis output given by equation (44), using the area formed outputs given by equation (47), and along with equation (15) yields $$\tilde{s}(r_{ij}, r, x_{ij}, x) = \qquad (52)$$

$$e^{-j\omega_c \frac{2r}{c}} S_{rcv}(x - x_{ij}, r_{ij}, r, \omega_c) \cdot \sum_{n=\underline{N}_{syn}(r_{ij})} \left\{h^{syn}(x_n - x_{ij}, r_{ij}, r_{xmt})\right.$$

$$\tilde{p}_{rcv}\left[\frac{2(r_{ij} - r)}{c} - \Delta T_{xmt}(x - x_n, r, r_{xmt}), x - x_n, r, r_{xmt}\right]$$

$$\left. e^{-j\omega_c \Delta T_{xmt}} S_{xmt}(x - x_n, r, r_{xmt}, \omega_c)\right\}$$

Note that for the image range location at which the target will appear, i.e., $$r_{ij} + \frac{c}{2}\Delta T_{xmt}(x - x_n, r, r_{xmt}),$$

the receive beampattern may contain a focusing error under the conditions described previously, and will be discussed in regard to the second transmit synthesis filter form. In order to determine a solution for the transmit synthesis filter coefficients, they may be derived based upon theoretical considerations, or an error function of the following form can be minimized, for each image location $(r_{ij},x_{ij})$, over point scatterer lateral locations x, using the list of potential range/position dependent $\underline{N}_{syn}(r_{ij},x_{ij})$ transmit beams, generally centered about the transmit beam closest to $x_{ij}$, i.e., $x_0(x_{ij})$:

$$\varepsilon^2 = \qquad (53)$$

$$\sum_x \left| \sum_{n=\underline{N}_{syn}(r_{ij})} \left\{ h^{syn}(x_n - x_{ij}, r_{ij}, r_{xmt})\tilde{p}_{rcv}[-\Delta T_{xmt}(x - x_n, r_{ij}, r_{xmt}), \right.\right.$$

$$x - x_n, r_{ij}, r_{xmt}] \cdot e^{-j\omega_c \Delta T_{xmt}(x-x_n, r_{ij}, r_{xmt})}$$

$$S_{xmt}(x - x_n, r_{ij}, r_{xmt}, \omega_c)\bigg\} -$$

$$p^{desired}(0, x - x_{ij}, r_{ij})S_{xmt}^{desired}(x - x_{ij}, r_{ij}, r_{xmt}, \omega_c) \bigg|^2 \quad \text{where}$$

$$p^{desired}\left[\frac{2(r_{ij} - r)}{c}, x - x_{ij}, r_{ij}\right]$$

and $s_{xmt}^{desired}(\ldots)$ are defined as the desired transmit pulse response and desired beampattern respectively, or taken together—the desired transmit point spread function, which is the targeted response for the spatial diffraction transform. r is evaluated at the image range coordinate $r_{ij}$. If $S_{xmt}^{desired}(\ldots)$ is that of a continuous focused transmit beam, then the subsequent transmit synthesis filter coefficients derived through error minimization or other means, will provide spatial compression of the transmit beam away from the focus, in addition to the spatial shifting property. Multiple image range locations $r_{ij}$ can also be used in evaluating $\tilde{p}_{rev}(\ldots)$, $S_{xmt}(\ldots)$, and $e^{-j\omega_c \Delta T_{xmt}}$ in equation (52), as well as $p^{desired}(\ldots)$ in forming the error function. Other error functions are possible. Evaluation of the receive pulse waveform(s) $\tilde{p}_{rev}(\ldots)$, transmit beampattern $s_{xmt}(\ldots)$, desired pulse response $p^{desired}(\ldots)$ and beampattern $S_{xmt}^{desired}(\ldots)$ and transmit differential time delay $\Delta T_{xmt}(\ldots)$ in the error minimization can be performed either through experimental measurement, simulation, or a combination thereof, provided they are sufficiently predictable. Applying the optimized transmit synthesis filter coefficients to the receive area formed output produces the round-trip point spread function $$\tilde{s}(r_{ij} - r, x_{ij} - x, r_{ij}, x_{ij}) \approx \qquad (54)$$

$$e^{-j\omega_c \frac{2r}{c}} \tilde{p}_{rcv}\left\{\frac{2(r_{ij} - r)}{c} - \Delta T_{xmt}[x_{ij} - x_0(x_{ij})], x - x_0(x_{ij}), r, r_{xmt}\right\} \cdot$$

$$S_{xmt}^{syn}(x - x_{ij}, r_{ij}, r, r_{xmt}, \omega_c)S_{rcv}(x - x_{ij}, r_{ij}, r, \omega_c)$$

which contains an approximate range displacement error of $$\frac{c}{2}\Delta T_{xmt}[x_{ij} - x_0(x_{ij})],$$

the round-trip point spread function's parameters are meant to indicate that it is in the form of a convolution kernel which could vary slowly throughout the imaging region, and where the synthesized transmit beampattern is given by $$S_{xmt}^{syn}(x - x_{ij}, r_{ij}, r, r_{xmt}, \omega_c) = \sum_{n=\underline{N}_{syn}(r_{ij})} h^{syn}(x_n - x_{ij}, r_{ij}, r_{xmt}) \quad (55)$$

$$e^{-j\omega_c \Delta T_{xmt}(x-x_n, r, r_{xmt})} S_{xmt}(x - x_n, r, r_{xmt}, \omega_c)$$

Note that the synthesized transmit beampattern is now centered over the image coordinate location $x_{ij}$ as described previously.

Substitution of the second form of $$h_n^{syn} = h^{syn}(x_n - x_{ij}, r_{ij}, r_{xmt})\delta\left[r_{ij} + \frac{c}{2}\Delta T_{xmt}(x_n - x_{ij}, r_{ij}, r_{xmt})\right]$$

into the transmit synthesis output given by equation (40), using the area formed outputs given by equation (47), and along with equation (15) yields $$\tilde{s}(r_{ij}, r, x_{ij}, x) = e^{-j\omega_c \frac{2r}{c}} \quad (56)$$

$$\sum_{n=\underline{N}_{syn}(r_{ij})} \left\{ h^{syn}(x_n - x_{ij}, r_{ij}, r_{xmt}) \tilde{p}_{rcv}\left[\frac{2(r_{ij} - r)}{c}, x - x_n, r, r_{xmt}\right]\right.$$

$$e^{-j\omega_c \Delta T_{xmt}} S_{xmt}(x - x_n, r, r_{xmt}, \omega_c)$$

$$\left. S_{rcv}\left[x - x_{ij}, r_{ij} + \frac{c}{2}\Delta T_{xmt}(x_n - x_{ij}, r_{ij}, r_{xmt}), r, \omega_c\right]\right\}$$

Note that while the range displacement error has been corrected—the transmit differential delay term no longer appears in the receive pulse response, the dependence of the synthesized round-trip point spread function $\tilde{s}(\ldots)$ on the receive beampattern is now transmit beam index n dependent due to the range displacement term $$\frac{c}{2}\Delta T_{xmt}(x_n - x_{ij}, r_{ij}, r_{xmt})$$

and introduces a receive focusing error given a sufficiently large differential transmit delay $\Delta T_{xmt}(x_n - x_{ij}, r_{ij}, r_{xmt})$. This can seen by evaluating the receive beampattern $S_{rcv}(\ldots)$ given by equation (50) at $$r_{ij} + \frac{c}{2}\Delta T_{xmt}(x_n - x_{ij}, r_{ij}, r_{xmt}).$$

Evaluating $r = r_{ij}$, it produces the phase error term $$e^{-j\omega_c \frac{u^2}{2c}}\left[\frac{1}{r_{ij}} - \frac{1}{r_{ij} + \frac{c}{2}\Delta T_{xmt}(x_n - x_{ij}, r_{ij}, r_{xmt})}\right] \quad (57)$$

If sufficiently large, this quadratic phase error term will lead to receive defocusing, which will also introduce a gain and phase modification of the receive beampattern contribution to equation (56). Whether or not the receive beampattern dependence needs to be included within the transmit synthesis coefficient solution depends upon whether the time shifts introduced by the differential transmit delay satisfy the following relationship.

$$R_{DOF}^{rcv} \sim \beta \lambda F_{rcv}^2, \quad 4 \leq \beta \leq 8 \quad (58)$$

$$\left|\frac{c}{2}\Delta T_{xmt}(x_n - x_{ij}, r_{ij}, r_{xmt})\right| \leq \frac{R_{DOF}^{rcv}}{2}$$

where the choice of) β depends upon what phase error is assumed at the end elements of the receive aperture in the depth of field (DOF) derivation. If the inequality in equation (58) is satisfied for image locations $(r_{ij}, x_{ij})$ and transmit beam location $x_n$ over transmit synthesis filters $\underline{N}_{syn}(r_{ij}, x_{ij})$, then the receive beampattern can be rearranged within the round-trip point spread function and is given by $$\tilde{s}(r_{ij}, r, x_{ij}) \approx e^{-j\omega_c \frac{2r}{c}} S_{rcv}[x - x_{ij}, r_{ij}, r, \omega_c]\cdot \quad (59)$$

$$\sum_{n=\underline{N}_{syn}(r_{ij})} h^{syn}(x_n - x_{ij}, r_{ij}, r_{xmt})\tilde{p}_{rcv}\left[\frac{2(r_{ij} - r)}{c}, x - x_n, r, r_{xmt}\right]$$

$$e^{-j\omega_c \Delta T_{xmt}} S_{xmt}(x - x_n, r, r_{xmt}, \omega_c)$$

from which the error function can be written as $$\varepsilon^2 \approx \sum_x \left| \sum_{n=\underline{N}_{syn}(r_{ij})} \left\{h^{syn}(x_n - x_{ij}, r_{ij}, r_{xmt})\tilde{p}_{rcv}(0, x - x_n, r_{ij}, r_{xmt}) \right.\right. \quad (60)$$

$$e^{-j\omega_c \Delta T_{xmt}(x-x_n, r_{ij}, r_{xmt})} S_{xmt}(x - x_n, r_{ij}, r_{xmt}, \omega_c)\} -$$

$$\left. p^{desired}(0, x - x_{ij}, r_{ij}) S_{xmt}^{desired}(x - x_{ij}, r_{ij}, r_{xmt}, \omega_c)\right|^2$$

where r is evaluated at the image range coordinate $r_{ij}$. Note that since the differential transmit delay $\Delta T_{xmt}(\ldots)$ has been corrected, there is no range displacement errors. As before, multiple image range locations $r_{ij}$ can be used in the error minimization. If the inequality in equation (58) is not satisfied, then the receive beampattern should be included in the transmit synthesis coefficient calculation procedure and/or error minimization. Applying the optimized transmit synthesis filter coefficients to the receive area formed output produces a round-trip point spread function given by $$\tilde{s}(r_{ij} - r, r, x_{ij} - x, r_{ij}, x_{ij}) \approx \quad (61)$$

$$e^{-j\omega_c \frac{2r}{c}} \tilde{p}_{rcv}\left[\frac{2(r_{ij} - r)}{c}, x - x_n, r, r_{xmt}\right] \cdot S_{xmt}^{syn}(x - x_{ij}, r_{ij}, r, r_{xmt}, \omega_c)$$

$$S_{rcv}(x - x_{ij}, r_{ij}, r, \omega_c)$$

where the synthesized transmit beampattern is given by $$S_{xmt}^{syn}(x - x_{ij}, r_{ij}, r, r_{xmt}, \omega_c) = \sum_{n=\underline{N}_{syn}(r_{ij})} h^{syn}(x_n - x_{ij}, r_{ij}, r_{xmt}) \quad (62)$$

$$e^{-j\omega_c \Delta T_{xmt}(x-x_n, r, r_{xmt})} S_{xmt}(x - x_n, r, r_{xmt}, \omega_c)$$

Substitution of the third form of $$h_n^{syn} = h^{syn}\left[x_n - x_{ij}, r_{ij} + \frac{c}{2}\Delta T_{xmt}(x_n - x_{ij}, r_{ij}, r_{xmt}), r_{xmt}\right]$$

into the transmit synthesis output given by equation (44), using the area formed outputs given by equation (47), and along with equation (15) yields $$\tilde{s}(r_{ij}, r, x_{ij}, x) = \quad (63)$$

$$e^{-j\omega_c \frac{2r}{c}} \sum_{n=\underline{N}_{syn}(r_{ij})} \left\{ \sum_{r'_{ij}} \left\{ h^{syn}(x_n - x_{ij}, r_{ij} - r'_{ij}, r_{ij}, r_{xmt}) \right. \right.$$

$$\left. \tilde{p}_{rcv}\left[\frac{2(r'_{ij} - r)}{c}, x - x_n, r, r_{xmt}\right] \cdot \right.$$

$$\left. S_{rcv}\left[x - x_{ij}, r'_{ij} + \frac{c}{2}\Delta T_{xmt}(x_n - x_{ij}, r'_{ij}, r_{xmt}), r, \omega_c\right] \right\}$$

$$\left. e^{-j\omega_c \Delta T_{xmt}} S_{xmt}(x - x_n, r, r_{xmt}, \omega_c) \right\}$$

where the extra $r_{ij}$ dependence in $h^{syn}(\ldots)$ is meant to indicate that the filter's range convolution kernel may change with image range $r_{ij}$ to compensate for the slow range dependence inherent in $\tilde{p}_{rcv}[\ldots, r, r_{xmt}]$. Note that while the range displacement error has been corrected—the transmit differential delay term no longer appears in the receive pulse response, the dependence of the synthesized round-trip point spread function $\tilde{s}(\ldots)$ on the receive beampattern is now transmit beam index n dependent due to the range displacement term $$\frac{c}{2}\Delta T_{xmt}(x_n - x_{ij}, r_{ij}, r_{xmt})$$

and introduces a receive focusing error given a sufficiently large differential transmit delay $\Delta T_{xmt}$ ($s_n$–$x_{ij}$,$r_{ij}$,$r_{xmt}$) as discussed previously. If the inequality in equation (58) is satisfied for image locations ($r_{ij}$,$x_{ij}$) and transmit beam location $x_n$ over transmit synthesis filters $\underline{N}_{syn}(r_{ij},x_{ij})$, and the range variation $r_{ij}$ of the receive beam pattern $S_{rcv}(\ldots)$ is slow compared with the time/range variation of $$\tilde{p}_{rcv}\left[\frac{2(r_{ij} - r)}{c}, \ldots\right],$$

which is generally the case unless long pulses combined with low receive F-numbers are used, then the receive beampattern can be rearranged within the synthesized round-trip point spread function and is given by $$\tilde{s}(r_{ij}, r, x_{ij}, x) \approx e^{-j\omega_c \frac{2r}{c}} S_{rcv}[x - x_{ij}, r_{ij}, r, \omega_c] \cdot \quad (64)$$

$$\sum_{n=\underline{N}_{syn}(r_{ij})} \sum_{r'_{ij}} \left\{ h^{syn}(x_n - x_{ij}, r_{ij} - r'_{ij}, r_{ij}, r_{xmt}) \tilde{p}_{rcv}\left[\frac{2(r'_{ij} - r)}{c}, \right. \right.$$

$$\left. \left. x - x_n, r, r_{xmt} \right] \right\} e^{-j\omega_c \Delta T_{xmt}} S_{xmt}(x - x_n, r, r_{xmt}, \omega_c)$$

Solving for the transmit synthesis filter coefficients assuming a finite number of range samples $r_m$, m=[0, 1, … M–1], evaluated around the nominal receive range r. The following error equation needs to be minimized, for each image location ($r_{ij}$,$x_{ij}$), over point scatterer lateral locations x and fast range/time $\hat{r}_{ij}$.

$$\varepsilon^2 = \quad (65)$$

$$\sum_{\hat{r}_{ij}} \sum_x \left| \sum_{n=\underline{N}_{syn}(r_{ij})} \left\{ \sum_{m'=0}^{M-1} \left\{ h^{syn}(x_n - x_{ij}, \hat{r}_{ij} - r_{m'}, r_{xmt}) \tilde{p}_{rcv}\left[\frac{2r_{m'}}{c}, x - \right. \right. \right. \right.$$

$$\left. \left. x_n, r_{ij}, r_{xmt} \right] \right\}$$

$$\left. e^{-j\omega_c \Delta T_{xmt}(x-x_n, r_{ij}, r_{xmt})} S_{xmt}(x - x_n, r_{ij}, r_{xmt}, \omega_c) \right\} -$$

$$\left. p^{desired}\left(\frac{2\hat{r}_{ij}}{c}, x - x_{ij}, r_{ij}\right) S_{xmt}^{desired}(x - x_{ij}, r_{ij}, r_{xmt}, \omega_c) \right|^2$$

Note that since the differential transmit delay $\Delta T_{xmt}(\ldots)$ has been corrected, there is no range displacement errors. In addition, the range/time dependence of the desired transmit pulse response $$p^{desired}\left(\frac{2\hat{r}_{ij}}{c}, x - x_{ij}, r_{ij}\right)$$

appears in the error minimization function. A set of simultaneous linear equations are created from the error function, and the unknown coefficients $h_{mn}^{syn}$=$h^{syn}$(m,n) are solved. If the inequality in equation (58) is not satisfied, or if long pulses are used in combination with low receive F-numbers, then the receive beampattern should be included in the transmit synthesis coefficient calculation procedure and/or error minimization. Applying the optimized transmit synthesis filter coefficients to the receive area formed output produces a synthesized round-trip point spread function given by $$s(r_{ij} - r, x_{ij} - x, r_{ij}, x_{ij}) \approx e^{-j\omega_c \frac{2r}{c}} p^{syn}\left[\frac{2(r_{ij} - r)}{c}, x - x_{ij}, r_{ij}\right] \quad (66)$$

$$S_{xmt}^{syn}(x - x_{ij}, r_{ij}, r, r_{xmt}, \omega_c) S_{rcv}(x - x_{ij}, r_{ij}, r, \omega_c)$$

where the synthesized transmit point spread function is given by $$p^{syn}\left[\frac{2(r_{ij}-r)}{c}, x-x_{ij}, r_{ij}\right] S_{xmt}^{syn}(x-x_{ij}, r_{ij}, r, r_{xmt}, \omega_c) \approx \qquad (67)$$

$$\sum_{n=\underline{N}_{syn}(r_{ij})} \sum_{m'=0}^{M-1} \left\{ h^{syn}(x_n-x_{ij}, r_{ij}, r_{xmt}) \tilde{p}_{rcv}\left[\frac{2r_{m'}}{c}, x-x_n, r, r_{xmt}\right] \right\}$$

$$e^{-j\omega_c \Delta T_{xmt}(x-x_n, r, r_{xmt})} S_{xmt}(x-x_n, r, r_{xmt}, \omega_c)$$

In the preceding analysis for both Image/Volume Reconstruction I and II, after obtaining the round-trip point spread function s( . . . ), assuming that linearity holds throughout the transmission, propagation, reception process, the pre-detected output $s_{out}(\ldots)$ can be found through the convolution of the round-trip point spread function with the region of interest scatterer density given by $$s_{out}(r_{ijk}) = \int \rho(\underline{r}')s(\underline{r}_{ijk}-\underline{r}',r_{ijk})d\underline{r}' \qquad (68)$$

where ρ(r) is the scatterer density.

Image/Volume Reconstruction I & II Hybrid

In both Image/Volume Reconstruction I & II architectures, additional information is being extracted from multiple channel data sets about the transmit beam's temporal and spatial properties, from the evolution of the transmit beam as it is swept through the region of interest, which provides the opportunity to refocus the transmit beam at all spatial locations, compensating for diffraction effects. Depending upon the particular implementation and desired requirements, either type I or II, or a hybrid of types I and II may be more suitable. For example, to avoid potential receive focusing errors as described in Image/Volume Reconstruction II, represented by FIG. 8, the receive dynamic delay term can include a transmit beam n and image coordinate dependent differential transmit delay correction in the Area/Volume Formation block directly. This creates a hybrid between the two architectures described, and may have other advantages in a particular implementation. Other rearrangements between the Transmit Synthesis and Area/Volume Formation blocks are possible.

Non-Linear Imaging Modes

Both Image/Volume Reconstruction architectures and techniques developed are able to synthesize a transmit beam of desired temporal and spatial characteristics, from a collection of actual transmit beams which possess potentially different temporal and spatial characteristics, thereby preserving the beneficial effects the actual transmit beams may have had in generating desirable imaging characteristics, while at the same time correcting for the undesirable characteristics after the fact on receive. This is especially important for non-linear imaging modes such as $2^{nd}$ harmonic imaging where the beneficial effects of clutter reduction come about due to the effective "squaring" of the transmit beam pattern which provides reduction of the transmit mainlobe width, lowering of the transmit beam clutter level, etc., subsequent to body aberrations. As stated previously, other techniques which seek to break up the transmit beam/aperture into several, or many, sequential components degrade this ability. While the examples provided assumed linearity throughout the analysis, non-linear imaging modes such as $2^{nd}$ harmonic imaging, etc., can be handled in a similar manner assuming that the scattering process is approximately linear. Since the transmit synthesis process occurs on the receive side following any non-linear transmit propagation, all that is required is an expression appropriate for describing the transmit pulse wavefront as it impinges upon the scatterer for the non-linear imaging mode of interest and simply inserting it into equation (17) instead of the one appropriate for linear, fundamental imaging. Alternatively, the transmit pulse wavefront for the non-linear imaging mode of interest can be expressed in terms of the linear, fundamental transmit pulse wavefront, either approximately or otherwise. For example, a reasonable model for $2^{nd}$ harmonic imaging might be $$\tilde{s}_{xmt}(t-T_{xmt}, x-x_n, r, r_{xmt}) = \tilde{p}^2(t-T_{xmt}, x-x_n, r, r_{xmt})e^{j2\omega_c(t-T_{xmt})} S_{xmt}^2(x-x_n, r, r_{xmt}, \omega_x) \qquad (69)$$

The evaluation of the non-linearly generated transmit beam pattern and pulse response in the subsequent transmit synthesis error minimization can be performed using measurements, simulations, theoretical considerations, or any combination thereof.

Computation Efficiency

The computation efficiency of the transmit synthesis technique described has advantages over other techniques which seek to provide a dynamic transmit focus. Consider for example, one of the techniques briefly described, namely transmit sub-apertures which breaks up the transmit aperture into many sub-apertures, which in the limit becomes that of a single transmit element. For each image point, the resulting receive channel signals are processed using delay, phase, apodization, and summation across transmit channels or firings, prior to delay, phase, apodization, and summation across receive channels. In general, to maintain constant resolution either on transmit or receive, the transmit and receive apertures need to increase as the focusing range increases. This implies that the number of computations involved, using operations such as delay, phase, and apodization in forming an image point, increases with the aperture size. For the sub-aperture technique, as shown in the left hand column of plots in FIG. 9, the transmit and receive aperture size increase linearly with depth r, with the product of the two being proportional to the number of operations needed to compute an image point at a particular depth r, which is given by a quadratic function.

Figure 9:
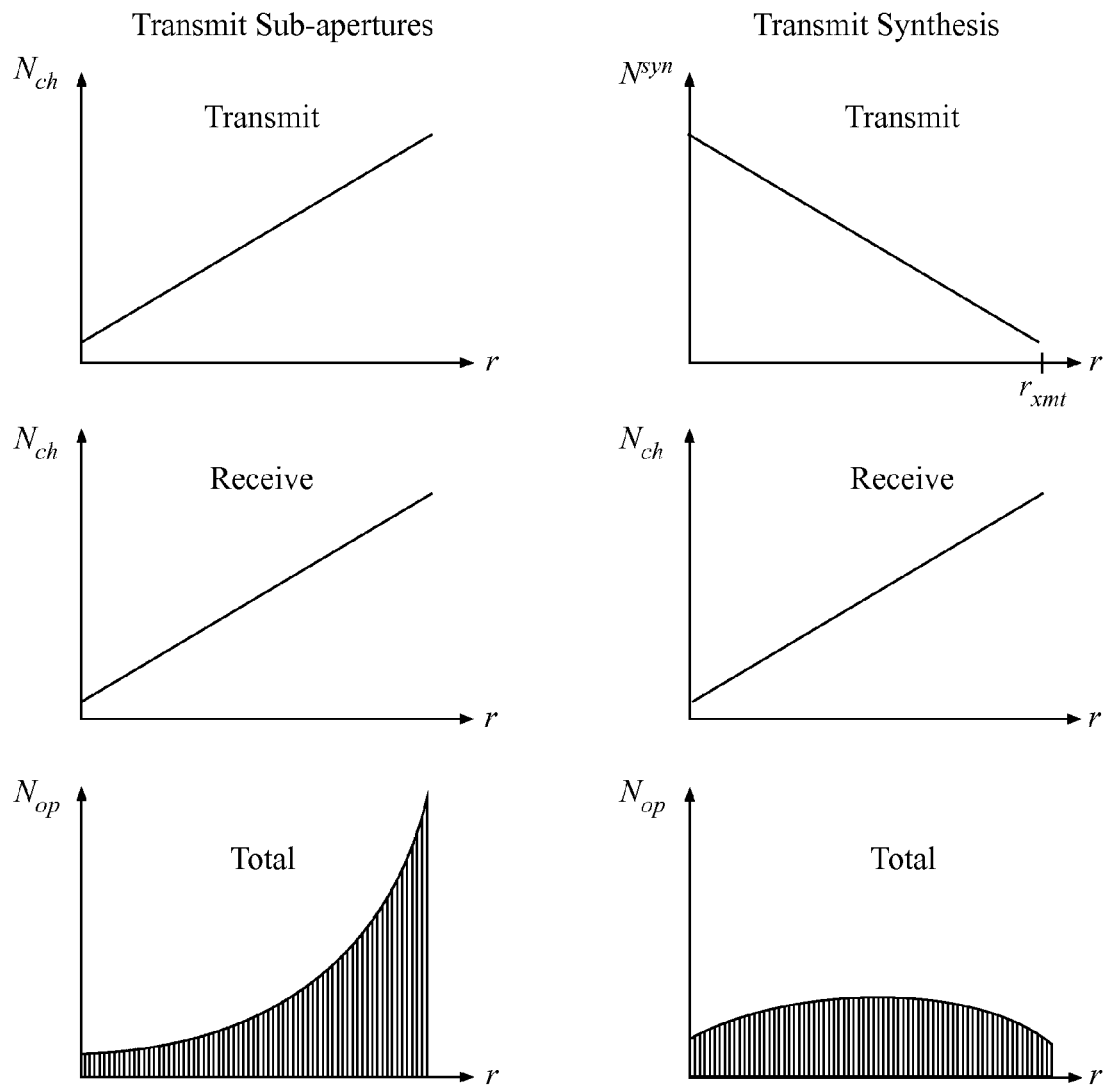
FIG. 9 shows plots of transmit, receive, and total computational effort for transmit sub-apertures and transmit synthesis to compare their computation efficiency.

The transmit synthesis technique described by the present invention can synthesize a dynamic transmit focus from a collection of conventionally focused transmit beams. The amount of spatial compression and hence, number of transmit synthesis filters $N^{syn}$ required to completely focus the transmit beam, is proportional to the range dependent width of the actual transmit beam. If the actual focus range is located towards the lower portion of the region of interest, which is typically the case, the number of transmit synthesis filters required is larger in the near field due to the defocused transmit beam width, decreasing with depth as the focus range $r_{xmt}$ is approached. At the focus range $r_{xmt}$, very few transmit synthesis filters are required, 2 or 3 suffice since the transmit beam is already focused, and the synthesis filters essentially provide the required spatial shifting of the transmit beam. Considering the spatial compression aspects only, the right hand column of plots in FIG. 9 show the number of computations involved in transmit synthesis and receive processing, with the product of the two being proportional to the number of operations needed to synthesize an image point at a particular depth r, which is also given by a quadratic function of a different shape (in the planar array example, the transmit synthesis filters used similar operations, namely delay, phase, and amplitude).

For the transmit sub-aperture technique, the number of operations continues to increase quadratically since the number of operations needed on transmit and receive both increase linearly with depth. In contrast, the transmit synthesis technique of the present invention, which uses more operations to synthesize a focused transmit beam in the near field and less operations to focus receive channels, and uses less operations to synthesize a focused transmit beam in the far field and more operations to focus receive channels, provides a better balancing of processing resources as shown in FIG. 9. If the total number of operations is computed by integrating the range dependent number of operations, shown by the patterned areas in the lower plots of FIG. 9, and if the range dependent transmit and receive apertures, along with the range dependent number of transmit synthesis filters are approximately given by $$N_{ch}^{xmt}(r) \sim \frac{1}{F_{xmt}d} r \tag{70}$$

$$N_{ch}^{xmt}(r) \sim \frac{1}{F_{xmt}d}(r_{xmt} - r)$$

$$N_{ch}^{rcv}(r) \sim \frac{1}{F_{rcv}d} r$$

$$N_{ch}^{rcv}(r) \sim \frac{1}{F_{rcv}d} r$$

$$N_{ops}^{sub}(r) \sim \frac{1}{F_{xmt}F_{rcv}d^2} r$$

$$N_{ops}^{sub}(r) \sim \frac{1}{F_{xmt}F_{rcv}d^2} r(r_{xmt} - r)$$

$$N_{ops}^{sub} \sim \int_0^{r_{xmt}} N_{ops}^{sub}(r) dr = \frac{1}{3F_{xmt}F_{rcv}d^2} r_{xmt}^2$$

$$N_{ops}^{sub} \sim \int_0^{r_{xmt}} N_{ops}^{sub}(r) dr = \frac{1}{6F_{xmt}F_{rcv}d^2} r_{xmt}^3$$

where d represents the transducer element spacing, then the ratio of computation effort for the present invention versus the sub-aperture technique is approximately given by $$\frac{N_{ops}^{syn}}{N_{ops}^{sub}} \sim \frac{\left(\frac{1}{6F_{xmt}F_{rcv}d^2} r_{xmt}^3\right)}{\left(\frac{1}{3F_{xmt}F_{rcv}d^2} r_{xmt}^3\right)} \tag{71}$$

$$\frac{N_{ops}^{syn}}{N_{ops}^{sub}} \sim \frac{1}{2}$$

The transmit synthesis technique described by the present invention needs approximately 50% fewer operations relative to the number of operations for the transmit sub-aperture technique.

Signal to Noise Ratio (SNR)

Figure 10:
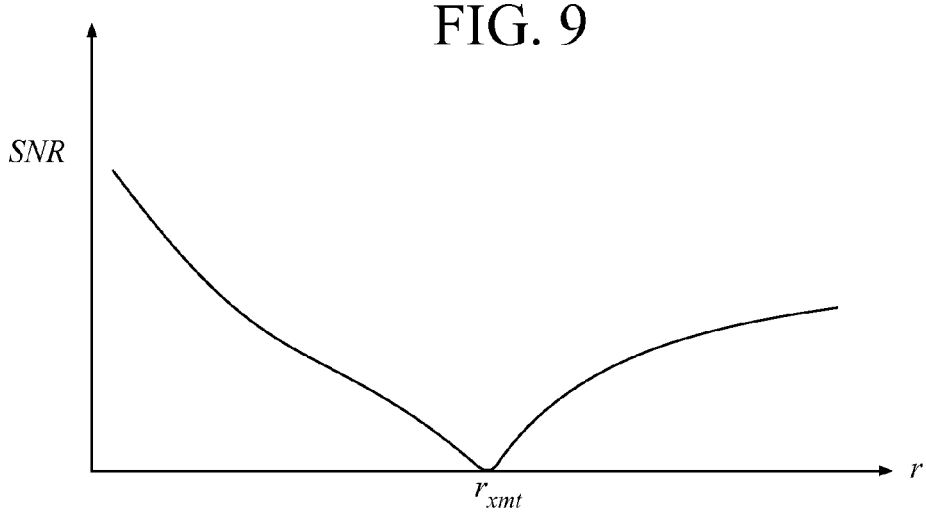
FIG. 10 is a plot of signal-to-noise ratio (SNR) showing improvement as a function of depth for transmit synthesis.

Since the transmit synthesis technique described by the present invention combines multiple sets of signals, i.e., channel data, area/volume formed data, beamformed data, etc., providing spatial compression to the diffracted transmit beam signals forming a continuous focused transmit beam, receive front-end random noise will be affected in a similar manner as in pulse compression techniques. In pulse compression techniques, the SNR is improved the most where the pulse has been the most dispersed. This implies that where the transmit beam is the most defocused, the greatest potential gain in SNR can be achieved, which will occur at depths shallow to and deeper than, the actual transmit focus. Around the transmit focus, the transmit beam will be modified to a much lesser degree, if at all, maintaining the SNR (dependent upon the particular design of the transmit synthesis filters). Thus, the SNR after transmit synthesis, whether performed on channel data or area formed data, can display an improvement as a function of depth as shown in FIG. 10. The SNR improvement using transmit synthesis performed in three dimensions, i.e., volume formation, should be even greater due to the added spatial compression dimension, i.e., elevation.

Scan Formats, 3-D Imaging Modes

The Reconstruction topologies and techniques developed by the present invention are able to synthesize a transmit beam of desired temporal and spatial characteristics, from a collection of actual transmit beams which possess potentially different temporal and spatial characteristics, where the collection of actual transmit beams { ... n−1 n n+1 ... } are swept through the region of interest in an arbitrary manner in 3-D space, either mechanically, electronically, or any combination thereof, making it compatible with all forms of scanning formats, i.e., linear, sector, curved, etc., employing transducers of arbitrary array geometries. The transducers employed can be 1-D arrays, 1½-D arrays, or 2-D arrays. The transmit synthesis compression can occur in an arbitrary 2-D plane, or 3-D space. All the preceding analysis is still valid—the image/volume coordinates used in the analysis are simply changed to ones appropriate for the describing spatial locations in 3-D space. The transmit synthesis error minimization may now contain additional spatial dimensions for optimization. For example, in the case of a linear scan format in both azimuth x and elevation y directions, the error minimization procedure to solve for the transmit synthesis filters now contains the added evaluation of the elevation beampattern along the y direction, in addition to the lateral x evaluation of the azimuth transmit beampattern, etc.

Motion Effects

Figure 11A:
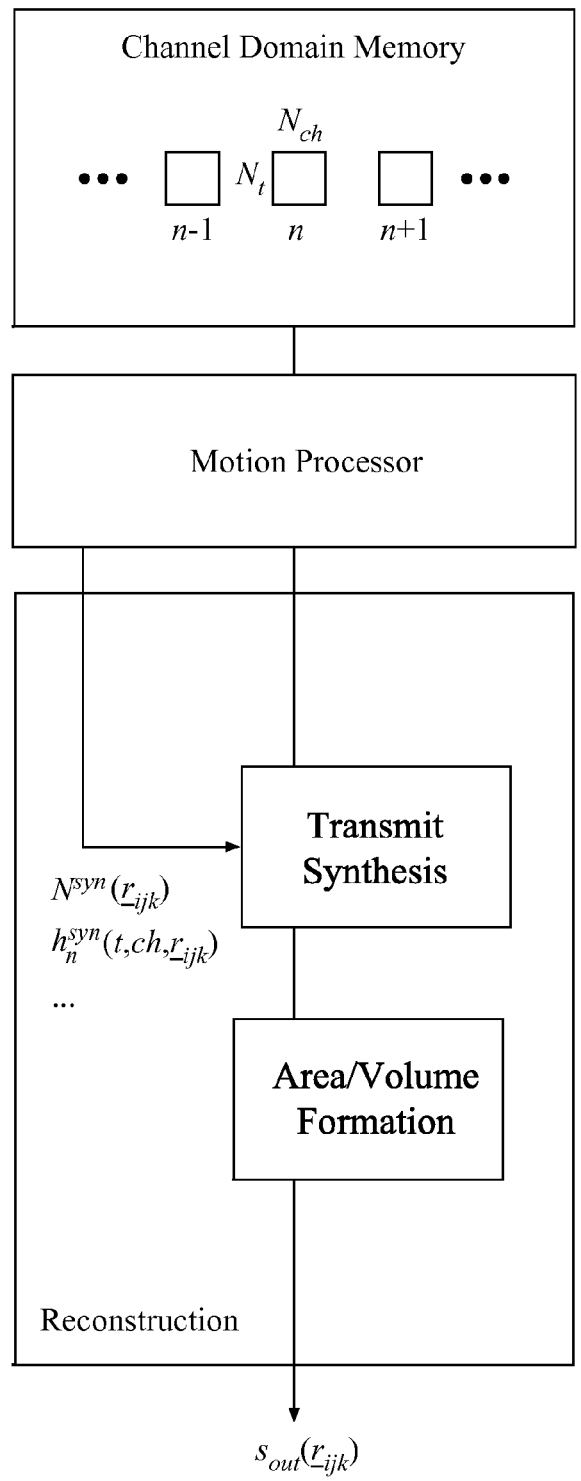
FIGS. 11A-11C show different arrangements of providing a motion processor block in the architecture topology of image/volume reconstruction to address motion effects.

In general, whenever signals are combined from multiple transmit firings, the potential exists for effects due to motion to alter the resulting signal combination, whether the signals are pre-detected or post-detected in origin. However, typically it is the case that pre-detected, or coherent, combination of signals will display greater changes due to the interference between the signals resulting from motion induced phase shifts. Since the present invention using transmit synthesis combines coherent signals from multiple transmit firings, the resulting spatial compression can be influenced by motion. Generally, the greater the number of signals combined from multiple transmit firings, the greater the potential sensitivity to motion. To the extent that motion induced effects are undesirable in the spatial compression process, which may not always be the case, several approaches can be employed to address motion effects. One approach is to change the amount of spatial compression employed, which is proportional to the number of transmit synthesis filters $h_{syn}(\ldots)$, which can be reduced accordingly, whether a priori in the design, or adaptive to the motion itself. A diagram of this process is shown in FIG. 11A where the Motion Processor block detects the motion from firing to firing employing channel data, and then computes appropriate parameters for the Transmit Synthesis block in order to reduce the sensitivity to motion such as through reduced number of transmit synthesis filters $N^{syn}$, filter definition $h_{syn}(\ldots)$, etc. The distinct advantage the present invention has over some other techniques such as transmit sub-apertures, is that the actual transmit beam used in data acquisition has already been formed in space, unaltered due to motion. Many transmit firings are not required to synthesize a transmit beam. The transmit synthesis process of the present invention spatially compresses the transmit beam away from the actual transmit focus, as well as aligning the transmit beam over the imaging point, to the extent that a) computational resources, i.e., number of transmit synthesis filters, are used to combine multiple coherent datasets, and b) motion, permit.

A second approach to address motion effects is to simply correct the data for motion induced spatial shifts in an adaptive manner. This can be accomplished through a variety of techniques well known in the field such as spatial correlation, either in 2-D or 3-D space. The data samples, either channel data or area/volume formed data, are spatially shifted and/or interpolated in an image, or volume position dependent manner, including any phase corrections for motion induced phase shifts, etc., prior to transmit synthesis processing. Thus any motion compensation processing would occur prior to the Transmit Synthesis block, or prior to the Reconstruction block, etc. This can also be represented by FIG. 11A where in this case, the Motion Processor block passes on motion corrected channel data to the Transmit Synthesis block. Note that the Transmit Synthesis block and Area/Volume Formation blocks can be interchanged, or the combination of the two modified as mentioned previously, in which case the Motion Processor block in FIG. 11A may be placed following the Area/Volume Formation block and prior to the Transmit Synthesis block. Other rearrangements are possible.

Figure 11B:
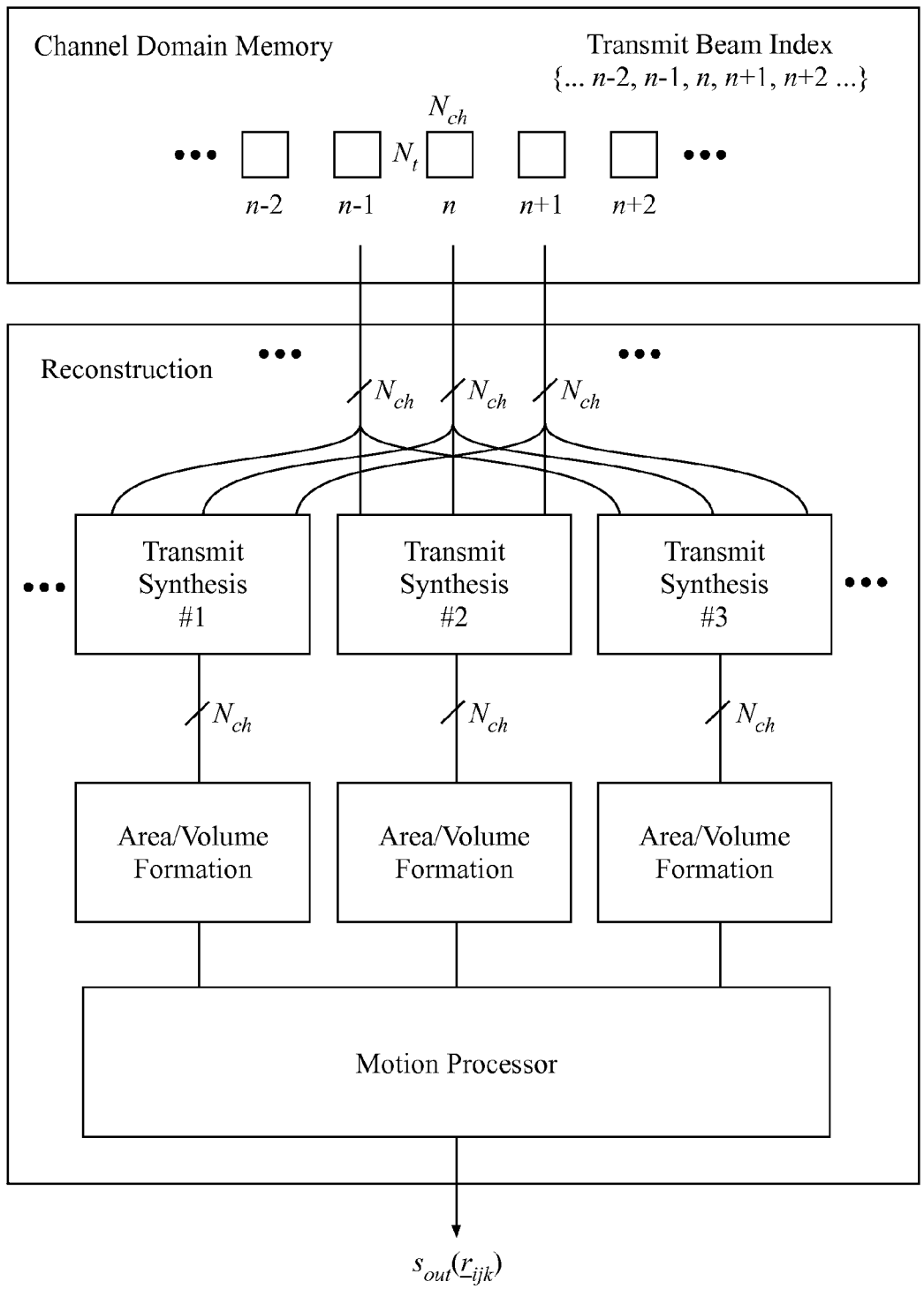
Figure 11C:
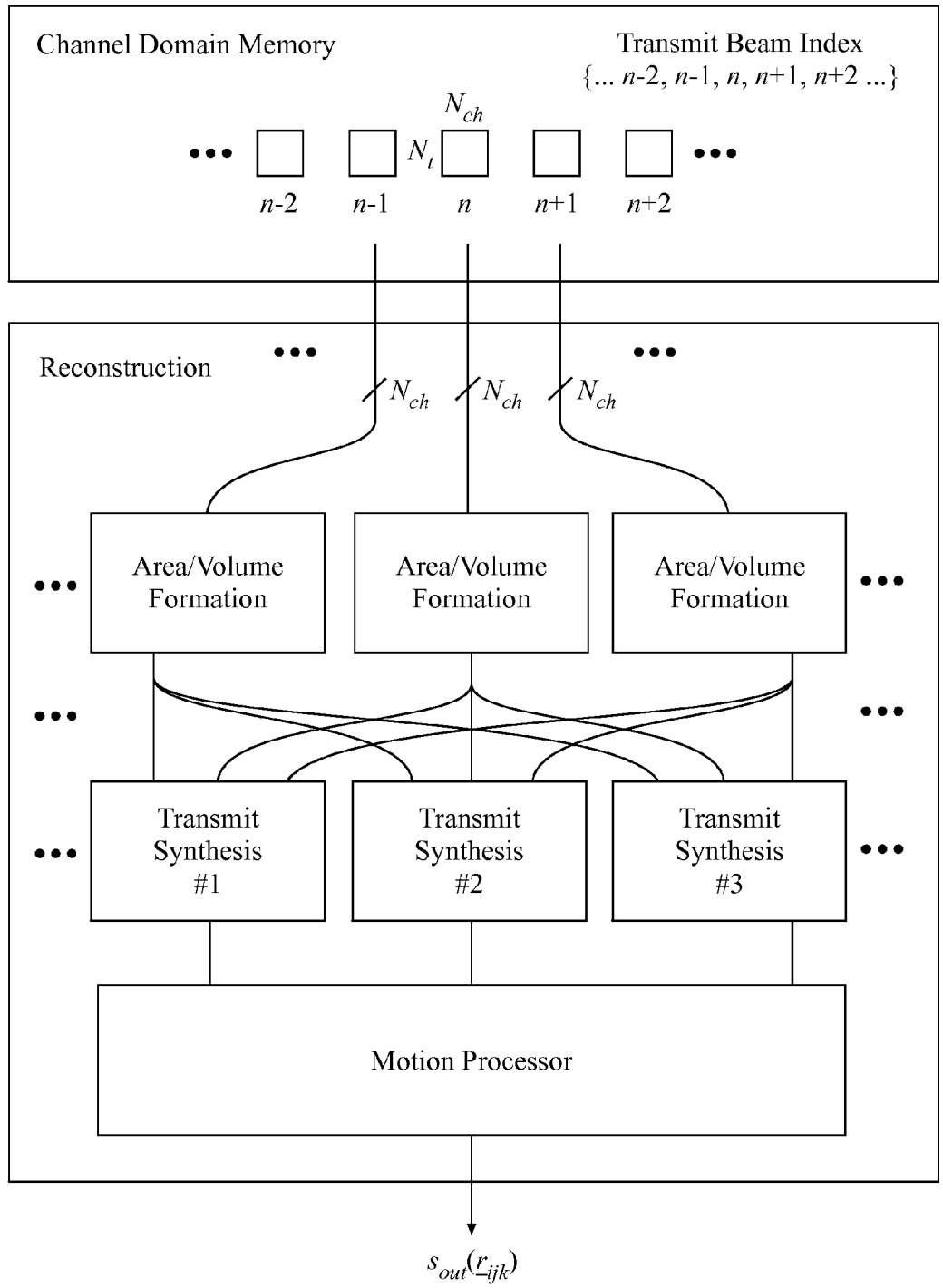

A third approach to address motion effects, which is also an adaptive technique, is to perform multiple transmit synthesis processing in parallel, using different sets of transmit synthesis filter designs $h_n^{syn}( \ldots )$, and combining each of the transmit synthesis outputs in a adaptive manner. For example, FIG. 11B and FIG. 11C represent this approach where multiple transmit synthesis outputs, either synthesized channel data sets, or synthesized area/volume formed outputs, are computed and are input to the Motion Processor block, which combines the multiple inputs in an adaptive manner, i.e., responsive to signal level, etc., to form a motion compensated output. Other rearrangements of the Transmit Synthesis, Area/Volume Formation, and Motion Processor blocks are possible as well as combining various aspects of FIG. 11A with FIGS. 11B and 11C.

Compatibility with Other Techniques

The transmit synthesis technique described is compatible with many other techniques used in ultrasound imaging.

(1) The transmit synthesis technique described by the present invention may be used in conjunction with many of the other techniques which seek to provide a dynamic transmit focus. For example, the technique of compositing multiple transmit foci in time along the same direction, however at different focal ranges, can be used with the transmit synthesis technique by spatially compressing the actual transmit beam around each transmit focal range using the receive signals acquired from each sequential transmit firing. In fact, if computational resources are limited, i.e., number of transmit synthesis filters, this provides a way in which to extend the transmit depth of field around each sequential transmit focal range using the spatial compression aspect of transmit synthesis of the present invention, and reduce the number of sequential focal ranges required to cover a given display depth. Transmit synthesis of the present invention also works in conjunction with other types of transmit beams, not simply those of a single fixed focus location. The actual transmit beams used may be of any type, namely transmit beams formed using composite transmit delay/phase/apodization profiles computed for different focal ranges, transmit beams formed by the linear superposition of transmit waveforms each of which are computed using different delay/phase/apodization profiles, different transmit waveforms for each element, etc.

(2) The transmit synthesis technique described by the present invention may be used in conjunction with transmit temporal coding techniques such as linear FM chirp waveforms, frequency/phase modulated waveforms, binary type codes such as Barker, Golay, etc. In fact, the actual decoding may be included within the transmit synthesis filters directly and depending upon the actual transmit synthesis-area/volume formation architecture, the decoding can operate on individual channel data which may improve the performance of the coding technique. Transmit synthesis of the present invention can be thought of as a type of spatial decoding where transmit diffraction away from the transmit focus has left the transmit beam incompletely decoded in a spatial sense. Thus, the addition of temporal decoding to the transmit synthesis filters creates a multi-dimensional decoding filter topology. In addition, orthogonal, or low cross-correlation codes may be employed for decoupling transmit beams fired simultaneously, thus improving the echo acquisition rate even further. The decoding may also be incorporated into the transmit synthesis filter topology, or kept as a separate processing step.

(3) The transmit synthesis technique described by the present invention may be used in conjunction with various forms of linear and non-linear imaging, with or without the addition of contrast agents. Transmit synthesis of the present invention can have distinct advantages in contrast agent imaging since in many cases, minimal contrast agent bubble destruction is desired. First, using the present invention of transmit synthesis, a reduced number of transmit firings are needed to adequately sample the image. Second, the temporal and spatial characteristics of the transmit beam used for acquisition can be suitably optimized for minimal bubble destruction. Then on the receive side, the present invention can synthesize a transmit beam of temporal and spatial characteristics optimized for imaging, for example increasing SNR in regions where the SNR resulting from the actual transmit beam was deficient, in order to minimize bubble destruction, etc.

(4) The transmit synthesis technique described by the present invention may be used in conjunction with aberration correction techniques which seek to correct the element-to-element delay/phase/apodization errors across the transducer array, on either transmit, receive, or both, associated with propagating through the layers of the body which may be of variable sound speed. Transmit synthesis of the present invention may improve the performance of the aberration correction techniques which make use of temporal cross correlations between receive channels by synthesizing a more focused transmit beam throughout the region of interest, which if performed prior to area/volume formation, will create a higher SNR, more correlated receive channel dataset from which to perform cross correlations. In addition, the element-to-element delay/phase/apodization corrections provided by the aberration correction algorithm can then be used to adapt the transmit synthesis filter values in order to improve the synthesized transmit beam's characteristics. This process can be repeated in an iterative manner if desired, improving both the transmit beam's characteristics, and element-to-element correlation, on each iteration.

(5) The transmit synthesis technique described by the present invention may be used in conjunction with sound speed correction techniques (see commonly assigned U.S. patent application Ser. No. 11/492,557, filed Jul. 24, 2006, entitled ABERRATION CORRECTION USING CHANNEL DATA IN ULTRASOUND IMAGING SYSTEM, which is incorporated herein by reference in its entirety) which seek to correct for the average, or bulk, sound speed of the body, i.e., the body sound speed may be lower or higher than the industry assumed standard of 1540 m/s. These techniques may generate multiple images assuming different sound speeds, where the generation of transmit beams, receive beams, or both, employ the assumed sound speeds. By quantitatively selecting the image for best focusing a suitable metric, an estimate of the body sound speed is obtained. The transmit synthesis filter values can then be modified in an adaptive manner making use of this estimated body sound speed, in order to provide a synthesized transmit beam of enhanced characteristics, i.e., better focusing properties, etc.

(6) The transmit synthesis technique described by the present invention may be used in conjunction with various forms of compounding, namely frequency compounding, spatial compounding, etc.

For all these techniques, as long as the pre-detected, i.e., coherent, temporal and spatial characteristics of the transmit beam(s) swept through the region of interest are sufficiently predictable, either through theory, measurement, or any combination thereof, then they may work in conjunction with transmit synthesis of the present invention.

The figures and examples provide in this disclosure are for illustrative purposes only and are not limited to the examples shown. While linear transmit synthesis filters and linear operations in area/volume formation were used in the examples, they are not limited to being linear in nature. The transmit synthesis filters and area/volume formation may make use of non-linear, or adaptive elements in order to enhance performance under various conditions.

It is to be understood that the above description is intended to be illustrative and not restrictive. Many embodiments will be apparent to those of skill in the art upon reviewing the above description. The scope of the invention should, therefore, be determined not with reference to the above description, but instead should be determined with reference to the appended claims along with their full scope of equivalents.

What is claimed is:

1. An ultrasound imaging method for achieving transmit and receive focusing at every echo location within a region of interest, the method comprising:
   providing a probe that includes one or more transducer elements for transmitting and receiving ultrasound waves;
   generating a sequence of spatially distinct transmit beams which differ in one or more of origin and angle;
   determining a transmit beam spacing substantially based upon a combination of actual and desired transmit beam characteristics, the transmit beam spacing being determined substantially without consideration of round-trip transmit-receive beam sampling requirements;
   storing coherent receive echo data, from two or more transmit beams of the spatially distinct transmit beams;
   combining coherent receive echo data from two or more transmit beams to achieve a substantially spatially invariant synthesized transmit focus at each echo location; and
   combining coherent receive echo data from each transmit firing to achieve dynamic receive focusing at each echo location.

2. The method of claim 1, wherein the probe is a 1-D or 2-D array with varying degrees of elevation beamforming control, including aperture, delay, and phase, or a general 2-D scanning array, or a sparse 1-D or 2-D array.

3. The method of claim 1, wherein the spatially distinct transmit beams are generated electronically, mechanically, or any combination thereof, to scan a 2-D plane or 3-D volume.

4. The method of claim 1, wherein coherent receive echo data is receive channel data from different transducer elements.

5. The method of claim 1, wherein combining coherent receive echo data from each transmit firing is performed prior to combining coherent receive echo data from two or more transmit beams.

6. The method of claim 5, wherein combining coherent receive echo data from each transmit firing is performed prior to storing coherent receive echo data.

7. The method of claim 1, wherein combining coherent receive echo data from each transmit firing is performed subsequent to combining coherent receive echo data from two or more transmit beams.

8. The method of claim 1, wherein combining coherent receive echo data from each transmit firing and combining coherent receive echo data from two or more transmit beams are performed simultaneously.

9. The method of claim 1, wherein combining coherent receive echo data from each transmit firing and combining coherent receive echo data from two or more transmit beams are performed at arbitrary echo locations or along multiple ray-like paths.

10. The method of claim 1, wherein one or more non-linear components of the transmitted ultrasound waves are included in the steps of storing coherent receive echo data, combining coherent receive echo data from each transmit firing, and combining coherent receive echo data from two or more transmit beams.

11. The method of claim 1, further comprising forming an image with an imaging mode that includes one or more of B, color Doppler, power Doppler, M, spectral pulsed-wave Doppler, with or without using contrast agents.

12. The method of claim 11, wherein velocity imaging modes including color velocity and spectral pulsed-wave Doppler are achieved using motion compensation in combining coherent receive echo data from two or more transmit beams.

13. The method of claim 11, wherein the spectral pulsed-wave Doppler mode involves processing one or more sample volumes along an arbitrary path in 2-D or 3-D space.

14. The method of claim 1, wherein combining coherent receive echo data from two or more transmit beams includes combining using one or more of delay, phase, amplitude, and convolution.

15. The method of claim 1, wherein combining coherent receive echo data from two or more transmit beams is responsive to echo location, as well as to the spatial and temporal characteristics of the actual and/or desired transmit beam characteristics, which includes one or more non-linear components of the transmitted ultrasound waves.

16. The method of claim 15, wherein combining coherent receive echo data from two or more transmit beams includes combining using one or more of delay, phase, amplitude, and convolution.

17. The method of claim 1, wherein the spatially distinct transmit beams differ in one or more of delay, phase, apodization, amplitude, frequency, or coding.

18. The method of claim 1, wherein the spatially distinct transmit beams have a single focus at a predetermined range, with an F-number ranging from 0.5 to 10.

19. The method of claim 1, wherein two or more of the spatially distinct transmit beams are fired simultaneously, or with a time gap less than a round-trip propagation time, for an even faster echo acquisition.

20. The method of claim 1, wherein the spatially distinct transmit beams are plane waves.

21. The method of claim 1, wherein the spatially distinct transmit beams are defocused.

22. The method of claim 1, and further comprising:
forming-two or more component images; and
compounding the two or more component images.

23. The method of claim 22, wherein the form of image compounding is that of frequency or spatial compounding.

24. An ultrasound imaging system for achieving transmit and receive focusing at every echo location within a region of interest, the system comprising:
- a probe that includes one or more transducer elements for transmitting and receiving ultrasound waves;
- means for generating a sequence of spatially distinct transmit beams which differ in one or more of origin and angle;
- means for determining a transmit beam spacing substantially based upon a combination of actual and desired transmit beam characteristics, the transmit beam spacing being determined substantially without consideration of round-trip transmit-receive beam sampling requirements;
- means for storing coherent receive echo data, from two or more transmit beams of the spatially distinct transmit beams;
- means for combining coherent receive echo data from two or more transmit beams to achieve a substantially spatially invariant synthesized transmit focus at each echo location; and
- means for combining coherent receive echo data from each transmit firing to achieve dynamic receive focusing at each echo location.

25. An ultrasound imaging system for achieving transmit and receive focusing at every echo location within a region of interest, the system comprising:
- a probe that includes one or more transducer elements for transmitting and receiving ultrasound waves; and
- a processor configured to:
  - generate a sequence of spatially distinct transmit beams which differ in one or more of origin and angle;
  - determine a transmit beam spacing substantially based upon a combination of actual and desired transmit beam characteristics, the transmit beam spacing being determined substantially without consideration of round-trip transmit-receive beam sampling requirements;
  - store coherent receive echo data, from two or more transmit beams of the spatially distinct transmit beams;
  - combine coherent receive echo data from two or more transmit beams to achieve a substantially spatially invariant synthesized transmit focus at each echo location; and
  - combine coherent receive echo data from each transmit firing to achieve dynamic receive focusing at each echo location.

26. An ultrasound imaging method for achieving transmit and receive focusing at every echo location within a region of interest, the method comprising:
- providing a probe that includes one or more transducer elements for transmitting and receiving ultrasound waves;
- generating a sequence of spatially distinct transmit beams which differ in one or more of origin and angle;
- determining a transmit beam spacing based upon a combination of actual and desired transmit beam characteristics, the transmit beam spacing being determined without consideration of round-trip transmit-receive beam sampling requirements;
- storing coherent receive echo data, from two or more transmit beams of the spatially distinct transmit beams;
- combining coherent receive echo data from two or more transmit beams to achieve a substantially spatially invariant synthesized transmit focus at each echo location; and
- combining coherent receive echo data from each transmit firing to achieve dynamic receive focusing at each echo location;
- wherein combining coherent receive echo data from each transmit firing is performed while simultaneously altering one or both of the synthesized transmit beam origin and the synthesized transmit beam angle through proper selection of one or more of delay, phase, amplitude, and convolution.

27. The method of claim 26, and further comprising:
forming-two or more component images; and
compounding the two or more component images.

28. The method of claim 27, wherein the form of image compounding is that of frequency or spatial compounding.

29. The method of claim 28, wherein one or more non-linear components of the transmitted ultrasound waves are included in the steps of storing coherent receive echo data.

30. The method of claim 29, and further comprising using one or more contrast agents in the region of interest.

* * * * *